US009480766B2

(12) United States Patent
Van Buskirk et al.

(10) Patent No.: US 9,480,766 B2
(45) Date of Patent: Nov. 1, 2016

(54) PHOTOCATALYTIC DEVICES AND SYSTEMS

(71) Applicants: Peter C. Van Buskirk, Newtown, CT (US); Jeffrey F. Roeder, Brookfield, CT (US)

(72) Inventors: Peter C. Van Buskirk, Newtown, CT (US); Jeffrey F. Roeder, Brookfield, CT (US)

(*) Notice: Subject to any disclaimer, the term of this patent is extended or adjusted under 35 U.S.C. 154(b) by 0 days.

(21) Appl. No.: 14/520,321

(22) Filed: Oct. 21, 2014

(65) Prior Publication Data

US 2015/0110679 A1    Apr. 23, 2015

Related U.S. Application Data

(60) Provisional application No. 61/893,823, filed on Oct. 21, 2013.

(51) Int. Cl.
| | |
|---|---|
| *A61L 9/00* | (2006.01) |
| *B01D 53/02* | (2006.01) |
| *B01J 21/06* | (2006.01) |
| *A61L 2/232* | (2006.01) |
| *A61L 2/238* | (2006.01) |

(52) U.S. Cl.
CPC ............... *A61L 9/00* (2013.01); *A61L 2/232* (2013.01); *A61L 2/238* (2013.01); *B01J 21/063* (2013.01)

(58) Field of Classification Search
CPC ........... A61L 9/00; A61L 9/03; A61L 9/205; F24F 13/28; F24F 3/16; B01J 19/123; B01J 35/004
USPC .................. 422/120, 122, 306; 95/273, 900; 55/482; 96/108, 224
See application file for complete search history.

(56) References Cited

U.S. PATENT DOCUMENTS

| | | | | |
|---|---|---|---|---|
| 2007/0059225 A1* | 3/2007 | Willette | .............. | A61L 9/16 422/186.3 |
| 2012/0201860 A1* | 8/2012 | Weimer | ............ | B01D 67/0002 424/400 |

OTHER PUBLICATIONS

A.P. Milnov, R.A. Fisher, A. Devi, "Synthesis, Characterization, and Thermal Properties of Homoleptic Rare-Earth Guanidinates: Promising Precursors for MOCVD and ALD of Rare-Earth Oxide Thin Films," Inorg. Chem. 47 (2008) 11405-11416. USA.

(Continued)

*Primary Examiner* — Monzer R Chorbaji
(74) *Attorney, Agent, or Firm* — Gregory Stauf

(57) ABSTRACT

Novel photocatalytic devices are disclosed, that utilize ultra-thin titania based photocatalytic materials formed on optical elements with high transmissivity, high reflectivity or scattering characteristics, or on high surface area or high porosity open cell materials. The disclosure includes methods to fabricate such devices, including MOCVD and ALD. The disclosure also includes photocatalytic systems that are either standalone or combined with general illumination (lighting) utility, and which may incorporate passive fluid exchange, user configurable photocatalytic optical elements, photocatalytic illumination achieved either by the general illumination light source, dedicated blue or UV light sources, or combinations thereof, and operating methodologies for combined photocatalytic and lighting systems. The disclosure also includes photocatalytic materials incorporated on the surface of packaged LEDs, LED lamps and LED luminaires, with photocatalytic materials incorporated on optically useful luminaire surfaces or on the surface of the remote phosphor. The disclosure also includes ultrathin photocatalytic materials incorporated on surfaces to affect antibacterial and antiviral properties.

38 Claims, 7 Drawing Sheets

(56) References Cited

OTHER PUBLICATIONS

J. McAleese, J.A. Darr, B.C.H. Steele, "The Synthesis and Thermal Evaluation of a Novel Cerium Precursor to Grow Thick Ceria Films by Metal-organic Chemical Vapor Deposition (MOCVD)," Chem. Vap. Dep. 2 (1996) 244-247. USA.
M. Becht, T. Gerfin, K.H. Dahmen, "Some Cerium beta-Diketonate Derivatives as MOCVD Precursors," Chem. Mater. 5 (1993) 137-144. USA.
J. Niinisto, N. Petrova, M. Putkonen, L. Niinisto, K. Artila, T. Sajavaara, "Gadolinium Oxide Thin Films by Atomic Layer Deposition," J. Cryst. Growth 285 (2005) 191-200. USA.
T. Gerfin, M. Beht, K.H. Dahmen, "Growth of Thin Films of Lanthanide Oxides and Lanthanide Copper Oxides by MOCVD," Ber. Bunsenges Phys. Chem. 95 (1991) 1564-1567. USA.
S. Liang, C.S. Chem, Z.Q. Shi, P. Lu, Y. Lu, B.H. Kear, "Control of CeO2 Growth by Chemical Vapor Deposition with a Special Source Evaporator," J. Cryst. Growth 151 (1995) 359-364. USA.
M. Pan, G.Y. Meng, H.W. Xin, C.S. Chen, D.K. Peng, Y.S. Lin, "Pure and Doped CeO2 Thin Films Prepared by MOCVD Process," Thin Sol. Films 324 (1998) 89-93. USA.
Z. Lu, R. Hiskes, S.A. Dicarolis, A. Nel, R.K. Route, R.S. Feigelson, Crystalline Quality and Surface Morphology of (100) CeO2 Thin Films Grown on Sapphire Substrates by Solid Source Metalorganic Chemical Vapor Deposition, J. Cryst. Growth 156 (1995) 227-234. USA.
Moussa, T. Conard, M.K. Van Bael, J.W. Maes, M. Jurczak, J.A. Kittl, S. Van Elshocht, "Atomic Layer Deposition of Gadolinium Aluminate using Gd(iPrCp)3, TMA, and O3 or H2O," Chem. Vap. Dep. 16 (2010) 170-178. USA.
L. Niinisto, J. Paivasaari, J. Niinisto, M. Putkonen, M. Nieminen, "Advanced Electronic and Optoelectronic Materials by Atomic Layer Deposition: An Overview with Special Emphasis on Recent Progress in Processing of high-k Dielectrics and Other Oxide Materials," Pys. Stat. Sol. A 201 (2004) 1443-1452. USA.
K.D. Pollard, H.A. Jenkins, R.J. Puddephat, Chemical Vapor Deposition of Cerium Oxide Using the Precursors [Ce(hfac)3(glyme)], Chem. Mater. 12 (2000) 701-710. USA.
W.H. Kim, M.K. Kim, W.J. Naeng, J. Gatineau, V. Pallen, C. Dussarrat, A. Noori, S. Thompson, S. Chu, H. Kim, "Growth Characteristics and Film Properties of Cerium Dioxide Prepared by Plasma-Enhanced Atomic Layer Deposition," J. Electrochem. Soc. 158 (2011) G169-G172. USA.
V. Miikkulainen, M. Leskela, M. Ritala, R.L. Puurunen, "Crystallinity of Inorganic Films Grown by Atomic Layer Deposition: Overview and General Trends," J. Appl. Phys. 113 (2013) 021301. USA.
M. Fanuciulli, G. Scarel, eds., Rare Earth Oxide Thin Films: Growth, Characterization, and Applications, Heidelburg: Springer 2007. USA.
J. Aarik, A. Aidla, H. Mandar, T. Uustare, "Atomic layer deposition of titanium dioxide from TiCl4 and H2O: investigation of growth mechanism," Appl. Surf. Sci 172 (2001) 148-158. USA.
J. Aarik, A. Aidla, T. Uustare, M. Ritala, M. Leskela, "Titanium isopropoxide as a precursor for atomic layer deposition: characterization of titanium dioxide growth process" Appl. Surf. Sci. 161 (2000) 385-395. USA.
A. Rahtu, M. Ritala, "Reaction Mechanism Studies on Titanium Isopropoxide—Water Atomic Layer Deposition Process," Chem. Vap. Dep. 8 (2002) 21-28. USA.
T. Alasaarela, T. Saastominen, J. Hiltunen, A. Saynatjoki, A. Tervonen, P. Stenberg, M. Kuittinen, S. Honkanen, "Atomic Layer Deposited Titanium Dioxide and its Application in Resonant Waveguide Grating," Appl. Optics 49 (2010) 4321-4325. USA.
M.L. Kaariainen, T.O. Kaariainen, D.C. Cameron, "Titanium dioxide thin films, their structure and its effect on their photoactivity and photocatalytic properties," Thin Sol. Films 517 (2009) 6666-6670. USA.

A. Sinha, D.W. Hess, C.L. Henderson, "Area selective atomic layer deposition of titanium dioxide: Effect of precursor chemistry," J. Vac. Sci. Technol. B24 (2006) 2523. USA.
K. Kukli, M. Ritala, M. Schuisky, M. Leskela, T. Sajavaara, J. Keinonen, T. Uustare, A. Harsta, Atomic Layer Deposition of Titanium Oxide from TiI4 and H2O2, Chem. Vap. Dep. 6 (2000) 303-310. USA.
M. Rose, J. Niinisto, P. Michalowski, L. Gerlich, L. Wilde, I. Endler, J.W. Bartha, "Atomic Layer Deposition of Titanium Dioxide Thin Films from Cp*Ti(OMe)3 and Ozone," J. Phys. Chem. C 113 (2009) 21825-21830. USA.
V. Pore, A. Rahtu, M. Leskela, M. Ritala, T. Sajavaara, J. Keinonen, "Atomic Layer Deposition of Photocatalytic TiO2 Thin Films from Titanium Tetramethoxide and Water," Chem, Vap. Dep. 10 (2004) 143-148. USA.
J. Heinrichs, T. Jarmar, M. Rooth, H. Engqvist, "In Vitro Bioactivity of Atomic Layer Deposited Titanium Dioxide on Titanium and Silicon Substrates," Key Engineering Materials: Bioceramics 23, G. Daculsi and P. Layrolle, eds. 2007, 689-692. USA.
A.P. Alekhin, S.A. Gudkova, A.M. Markeev, A.S. Mitiaev, A.A. Sigarev, V.F. Toknova, "Structural Properties of the Titanium Dioxide Thin Films Grown by Atomic Layer Deposition at Various Numbers of Reaction Cycles," Appl. Surf. Sci. 257 (2010) 186-191. USA.
D.H. Kim, H.J. Koo, J.S. Jur, M. Woodroof, B. Kalanyan, K. Lee, C.K. Devine, G.N. Parsons, "Stable Anatase TiO2 Coating on Quartz Fibers by Atomic Layer Deposition for Photoactive Light Scattering in Dye Sensitized Solar Cells," Nanoscale 4 (2012) 4731-4738. USA.
M.D. McDaniel, A. Posadas, T. Wang, A.A. Demkov, J.G. Ekerdt, "Growth and Characterization of Epitaxial Anatage TiO2 (001) on SrTiO3 buffered Si (001) Using Atomic Layer Deposition," Thin Sol. Films 520 (2012) 6525-6530. USA.
C.S. Lee, J. Kim, J.Y. Son, W.J. Maeng, D.H. Ji, W. Choi, H. Kim, "Plasma-Enhanced ALD of TiO2 Thin Films on SUS 304 Stainless Steel for Photocatalytic Application," J. Electrochem. Soc. 156 (2009) D188-D192. USA.
W.J. Maeng, H. Kim, "Thermal and Plasma-Enhanced ALD of Ta and Ti Oxide Thin Films froAlkylamide Precursors," Electrochem. Solid-State Lett. 9 (2006) G191-G194. USA.
M.C.K. Sellers, E.G. Seebauer, "Structural and Magnetic Properties of Mn-doped Anatase TiO2 Films Synthesized by Atomic Layer Deposition," Appl. Phys. A 104 (2011) 583-586. USA.
A. Sakar, S. Potts, S. Rushworth, F. Roozeboon, M.C.M. Van De Sandene, W.M.M Kessel, "Plasma-Enhanced ALD of TiO2 Using a Novel Cyclopentadienyl Alkylamido Precursor [Ti(CpMe)(NMe2)3 and O2 Plasma," ECS Trans. 33 (2010) 385-393. USA.
H.E. Chen, C.M. Hsu, Y.C. Chen, "Substrate Materials and Deposition Temperature Dependent Growth Characteristics and Photocatalytic Properties of ALD TiO2 Films," J. Electrochem. Soc. 156 (2009) D275-D278. USA.
http://www.cdc.gov/hai/progress-report/index.html USA.
David J. Webera, Deverick Anderson, William A. Rutala, "The role of the surface environment in healthcare associated infections", Infectious Diseases, 26 (4), 2013 USA.
D.J. Weber, W.A. Rutala, M.B. Miller, K. Huslage, E. Sickbert-Bennet, "Role of hospital surfaces in the transmission of emerging health care-associated pathogens: norovirus, Clostridium difficile, and Acinetobacter species" Am J Infect Control 2010;38:S25-S33. USA.
"Stomach illness that hit 83 people on cruise ship may be linked to norovirus", CNN, Apr. 10, 2014 USA.
K. Huslage, William A. Rutala, MPH, Maria F. Gergen, Emily Sickbert-Bennet, David J. Weber, "Microbial Assessment of High-, Medium-,and Low-Touch Hospital Room Surfaces", Infection Control and Hospital Epidemiology, vol. 34, No. 2 (Feb. 2013), pp. 211-212 USA.
R. Nakano, et al., "Broad Spectrum Microbiocidal Activity of Photocatalysis by TiO2", Catalysts 2013, 3, pp. 310-323 USA.

(56) References Cited

OTHER PUBLICATIONS

S.M. George, "Atomic Layer Deposition: An Overview," Chem. Rev. 110 (2010) 111-131. USA.

Kirk Huslage, William A. Rutala, Emily Sickbert-Bennett, David J. Weber, "A Quantitative Approach to Defining "High-Touch" Surfaces in Hospitals", Infection Control and Hospital Epidemiology, 31 (8) Aug. 2010 USA.

Koichi Awazu, Makoto Fujimaki, Carsten Rockstuhl, Junji Tominaga, Hirotaka Murakami, Yoshimichi Ohki, Naoya Yoshida, Toshiya Watanabe, "A Plasmonic Photocatalyst Consisting of Silver Nanoparticles Embedded in Titanium Dioxide",J. Am. Chem. Soc. 130, 1676-1680 (2008) USA.

A. Fujishima, K. Honda, S. Kikuchi, "Photosensitized electrolytic oxidation on semiconducting $TiO_2$ electrode", Kogoyo Kagaku 72, pp. 108-113 (1969) USA.

S.M. Gupta, M. Tripathy, "A Review of $TiO_2$ nanoparticles", Chinese science Bulletin, 56 (16) 1639-57 (2011) USA.

U. Diebold, The surface science of titanium dioxide, Surface Science Reports, vol. 48, Issues 5-8, Jan. 2003, pp. 53-229 USA.

P.S.M. Dunlop et al., "Inactivation of clinically relevant pathogens by photocatalytic coatings", J. Photochemistry and Photobiology A, 216, 303-310 (2010). USA.

A. Kubacka et al., "Understanding the antimicrobial mechanism of $TiO_2$-based nanocomposite films in a pathogenc bacterium", Scientific Reports, 4, 4134 (2014). USA.

* cited by examiner

PHOTOCATALYTIC DEVICES AND SYSTEMS

CROSS REFERENCE TO RELATED APPLICATIONS

This application is a U.S. Utility application taking priority from U.S. Provisional application No. 61/893,823 filed Oct. 21, 2013, and herein incorporated by reference.

FIELD OF THE INVENTION

The present invention relates to novel photocatalytic devices, fabrication methods for those devices, and novel systems that combine lighting and photocatalytic air purification functions.

BACKROUND

References

A. P. Milnov, R. A. Fisher, and A. Devi, "Synthesis, Characterization, and Thermal Properties of Homoleptic Rare-Earth Guanidinates: Promising Precursors for MOCVD and ALD of Rare-Earth Oxide Thin Films," Inorg. Chem. 47 (2008) 11405-11416.

J. McAleese, J. A. Darr, and B. C. H. Steele, "The Synthesis and Thermal Evaluation of a Novel Cerium Precursor to Grow Thick Ceria Films by Metal-organic Chemical Vapor Deposition (MOCVD)," Chem. Vap. Dep. 2 (1996) 244-247.

M. Becht, T. Gerfin, and K-H. Dahmen, "Some Cerium-Diketonate Derivatives as MOCVD Precursors," Chem. Mater. 5 (1993) 137-144.

J. Niinisto, N. Petrova, M. Putkonen, L. Niinisto, K. Arstila, and T. Sajavaara, "Gadolinium Oxide Thin Films by Atomic Layer Deposition," J. Cryst. Growth 285 (2005) 191-200.

T. Gerfin, M. Becht, and K-H. Dahmen, "Growth of Thin Films of Lanthanide Oxides and Lanthanide Copper Oxides by MOCVD," Ber. Bunsenges Phys. Chem. 95 (1991) 1564-1567.

S. Liang, C. S. Chern, Z. Q. Shi, P. Lu, Y. Lu, and B. H. Kear, "Control of CeO2 Growth by Chemical Vapor Deposition with a Special Source Evaporator," J. Cryst. Growth 151 (1995) 359-364.

M. Pan, G. Y. Meng, H. W. Xin, C. S. Chen, D. K. Peng, and Y. S. Lin, "Pure and Doped CeO2 Thin Films Prepared by MOCVD Process," Thin Sol. Films 324 (1998) 89-93.

Z. Lu, R. Hiskes, S. A. DiCarolis, A. Nel, R. K. Route, and R. S. Feigelson, "Crystallin Quality and Surface Morphology of (100) CeO2 Thin Films Grown on Sapphire Substrates by Solid Source Metalorganic Chemical Vapor Deposition, J. Cryst. Growth 156 (1995) 227-234.

C. Adelmann, D. Piereux, J. Swerts, D. Dewulf, A. Hardy, H. Tielens, A. Franquet, B. Brijs, A. Moussa, T. Conard, M. K. Van Bael, J. W. Maes, M. Jurczak, J. A. Kittl, and S. Van Elshocht, "Atomic Layer Deposition of Gadolinium Aluminate using Gd(iPrCp)3, TMA, and O3 or H2O," Chem. Vap. Dep. 16 (2010) 170-178.

L. Niinisto, J. Paivasaari, J. Niinisto, M. Putkonen, and M. Nieminen, "Advanced Electronic and Optoelectronic Materials by Atomic Layer Deposition: An Overview with Special Emphasis on Recent Progress in Processing of high-k Dielectrics and Other Oxide Materials," Pys. Stat. Sol. A 201 (2004) 1443-1452.

K. D. Pollard, H. A. Jenkins, and R. J. Puddephat, "Chemical Vapor Deposition of Cerium Oxide Using the Precursors [Ce(hfac)3(glyme)]," Chem. Mater. 12 (2000) 701-710.

W-H. Kim, M-K. Kim, W. J. Naeng, J. Gatineau, V. Pallen, C. Dussarrat, A. Noori, S. Thompson, S. Chu, and H. Kim, "Growth Characteristics and Film Properties of Cerium Dioxide Prepared by Plasma-Enhanced Atomic Layer Deposition," J. Electrochem. Soc. 158 (2011) G169-G172.

S. M. George, "Atomic Layer Deposition: An Overview," Chem. Rev. 110 (2010) 111-131.

V. Miikkulainen, M. Leskela, M. Ritala, and R. L. Puurunen, "Crystallinity of Inorganic Films Grown by Atomic Layer Deposition: Overview and General Trends," J. Appl. Phys. 113 (2013) 021301.

M. Fanuciulli and G. Scarel, eds., Rare Earth Oxide Thin Films: Growth, Characterization, and Applications, Heidelburg: Springer 2007.

J. Aarik, A. Aidla, H. Mändar, and T. Uustare, "Atomic layer deposition of titanium dioxide from TiCl4 and H2O: investigation of growth mechanism," Appl. Surf. Sci 172 (2001) 148-158.

J. Aarik, A. Aidla, T. Uustare, M. Ritala, and M. Leskela, "Titanium isopropoxide as a precursor for atomic layer deposition: characterization of titanium dioxide growth process" Appl. Surf. Sci. 161 (2000) 385-395.

A. Rahtu and M. Ritala, "Reaction Mechanism Studies on Titanium Isopropoxide-Water Atomic Layer Deposition Process," Chem. Vap. Dep. 8 (2002) 21-28.

T. Alasaarela, T. Saastominen, J. Hiltunen, A. Saynatjoki, A. Tervonen, P. Stenberg, M. Kuittinen, and S. Honkanen, "Atomic Layer Deposited Titanium Dioxide and its Application in Resonant Waveguide Grating," Appl. Optics 49 (2010) 4321-4325.

M.-L. Kääriäinen, T. O. Kääriäinen, D. C. Cameron, "Titanium dioxide thin films, their structure and its effect on their photoactivity and photocatalytic properties," Thin Sol. Films 517 (2009) 6666-6670.

A. Sinha, D. W. Hess, and C. L. Henderson, "Area selective atomic layer deposition of titanium dioxide: Effect of precursor chemistry," J. Vac. Sci. Technol. B24 (2006) 2523.

K. Kukli, M. Ritala, M. Schuisky, M. Leskela, T. Sajavaara, J. Keinonen, T. Uustare and A. Hårsta, "Atomic Layer Deposition of Titanium Oxide from TiI4 and H2O2, Chem. Vap. Dep. 6 (2000) 303-310.

M. Rose, J. Niinisto, P. Michalowski, L. Gerlich, L. Wilde, I. Endler, and J. W. Bartha, "Atomic Layer Deposition of Titanium Dioxide Thin Films from Cp*Ti(OMe)3 and Ozone," J. Phys. Chem. C 113 (2009) 21825-21830.

V. Pore, A. Rahtu, M. Leskela, M. Ritala, T. Sajavaara, and J. Keinonen, "Atomic Layer Deposition of Photocatalytic TiO2 Thin Films from Titanium Tetramethoxide and Water," Chem, Vap. Dep. 10 (2004) 143-148.

J. Heinrichs, T. Jarmar, M. Rooth, H. Engqvist, "In Vitro Bioactivity of Atomic Layer Deposited Titanium Dioxide on Titanium and Silicon Substrates," Key Engineering Materials: Bioceramics 23, G. Daculsi and P. Layrolle, eds. 2007, 689-692.

A. P. Alekhin, S. A. Gudkova, A. M Markeev, A. S. Mitiaev, A. A. Sigarev, and V. F. Toknova, "Structural Properties of the Titanium Dioxide Thin Films Grown by Atomic Layer Deposition at Various Numbers of Reaction Cycles," Appl. Surf. Sci. 257 (2010) 186-191.

D. H. Kim, H-J Koo, J. S. Jur, M. Woodroof, B. Kalanyan, K. Lee, C. K. devine, and G. N. Parsons, "Stable Anatase TiO2 Coating on Quartz Fibers by Atomic Layer Deposition for Photoactive Light Scattering in Dye Sensitized Solar Cells," Nanoscale 4 (2012) 4731-4738.

M. D. McDaniel, A. Posadas, T. Wang, A. A. Demkov, and J. G. Ekerdt, "Growth and Characterization of Epitaxial Anatage TiO2 (001) on SrTiO3 buffered Si (001) Using Atomic Layer Deposition," Thin Sol. Films 520 (2012) 6525-6530.

C-S. Lee, J. Kim, J. Y. Son, W. J. Maeng, D-H Ji, W. Choi, and H. Kim, "Plasma-Enhanced ALD of TiO2 Thin Films on SUS 304 Stainless Steel for Photocatalytic Application," J. Electrochem. Soc. 156 (2009) D188-D192.

W. J. Maeng and H. Kim, "Thermal and Plasma-Enhanced ALD of Ta and Ti Oxide Thin Films froAlkylamide Precursors," Electrochem. Solid-State Lett. 9 (2006) G191-G194.

M. C. K. Sellers and E. G. Seebauer, "Structural and Magnetic Properties of Mn-doped Anatase TiO2 Films Synthesized by Atomic Layer Deposition," Appl. Phys. A 104 (2011) 583-586.

A. Sakar, S. Potts S. Rushworth, F. Roozeboon, M. C. M Van De Sandene, and W. M. M. Kessel, "Plasma-Enhanced ALD of TiO2 Using a Novel Cyclopentadienyl Alkylamido Precursor [Ti(CpMe)(NMe2)3 and O2 Plasma," ECS Trans. 33 (2010) 385-393.

H-E Chen, C-M Hsu, and Y-C. Chen, "Substrate Materials and Deposition Temperature Dependent Growth Characteristics and Photocatalytic Properties of ALD TiO2 Films," J. Electrochem. Soc. 156 (2009) D275-D278.

http://www.cdc.gov/hai/progress-report/index.html

David J. Webera, Deverick Anderson, and William A. Rutala, "The role of the surface environment in healthcare associated infections", Infectious Diseases, 26 (4), 2013

Weber D J, Rutala W A, Miller M B, Huslage K, Sickbert-Bennett E. "Role of hospital surfaces in the transmission of emerging health care-associated pathogens: norovirus, *Clostridium difficile*, and *Acinetobacter* species" Am J Infect Control 2010; 38:S25-S33.

"Stomach illness that hit 83 people on cruise ship may be linked to norovirus", CNN, Apr. 10, 2014

Huslage, K., William A. Rutala, W. A., MPH; Maria F. Gergen, M. F. Emily E. Sickbert-Bennett, E., David J. Weber, "Microbial Assessment of High-, Medium-, and Low-Touch Hospital Room Surfaces", Infection Control and Hospital Epidemiology, Vol. 34, No. 2 (February 2013), pp. 211-212

Nakano, R. et al., "Broad Spectrum Microbiocidal Activity of Photocatalysis by TiO2", Catalysts 2013, 3, pp. 310-323

R. Nakano et al., "Broad Spectrum Microbicidal Activity of Photocatalysis by TiO2", Catalysts 2013, 3, 310-323

Kirk Huslage, William A. Rutala, Emily Sickbert-Bennett, David J. Weber, "A Quantitative Approach to Defining "High-Touch" Surfaces in Hospitals", Infection Control and Hospital Epidemiology, 31 (8) August 2010

Koichi Awazu, Makoto Fujimaki, Carsten Rockstuhl, Junji-Tominaga, Hirotaka Murakami, Yoshimichi Ohki, Naoya Yoshida and Toshiya Watanabe, "A Plasmonic Photocatalyst Consisting of Silver Nanoparticles Embedded in Titanium Dioxide", J. AM. Chem. Soc. 130, 1676-1680 (2008)

A. Fujishima, K. Honda, S. Kikuchi, "Photosensitized electrolytic oxidation on semiconducting TiO2 electrode", Kogoyo Kagaku 72, pp 108-113 (1969)

S. M. Gupta, M. Tripathy, "A Review of TiO2 nanoparticles", Chinese science Bulletin, 56 (16) 1639-57 (2011)

U. Diebold, The surface science of titanium dioxide, Surface Science Reports, Volume 48, Issues 5-8, January 2003, Pages 53-229

P. S. M. Dunlop et al., "Inactivation of clinically relevant pathogens by photocatalytic coatings", J. Photochemistry and Photobiology A, 216, 303-310 (2010)

A. Kubacka et al., "Understanding the antimicrobial mechanism of TiO2-based nanocomposite films in a pathogenc bacterium", Scientific Reports, 4, 4134 (2014)

The plethora of chemical contaminants in our environment is a major concern, and their deleterious health effects are only partially understood but believed to be enormous. Commercially practical techniques for removal of these contaminants are therefore of great interest. Examples of contaminants include, but are by no means limited to formaldehydes, aromatic hydrocarbons, various mitogen oxides, pesticides, specific bacteria, viruses, etc.

Titanium dioxide is the archetypal photocatalyst, due to its highly oxidizing properties when irradiated by UV light, physical robustness, insolubility in water, low cost, low toxicity and other attributes. Photocatalysis using titanium dioxide (titania, TiO2) has received huge interest for purifying gases and fluids, in particular air and aqueous fluids, via oxidizing chemical reactions at a surface, via creation of electron-electron hole pairs.

A wide variety of titania-based materials, doping schemes, physical configurations have been proposed to enhance and utilize photocatalysis at TiO2 surfaces, although so far there has not been widespread adoption of the technology for purification of air, fluids or surfaces. The inventors of the present invention believe that several technical and economic factors have reduced the utility, effectiveness, commercial viability of photocatalytic air purification systems.

Photocatalysis is typically achieved by a low or medium pressure UV lamp, or in some cases a Xenon lamp, irradiating the front surface of a ceramic or powder based titania surface, i.e. from the direction of the medium that is targeted to be purified. UV LEDs have also been employed, although these devices typically have very short product lifetimes and are unreliable.

Photocatalysis utilizing titanium dioxide is typically excited by illumination in the UV or near UV 240-400 nm spectral region, which is hazardous to humans, more technologically complicated and more expensive than visible light based illumination sources.

Other challenges with conventional standalone photocatalytic systems include the difficulty of uniform radiation, purification media (i.e. media to be purified) interfering with illumination, high voltage lamp power supplies and control, mercury content in the lamp, air exchange and the large system sizes. The need for a dedicated illumination source increases system complexities and therefore reduces the viability of commercial devices.

The chemical activation at the surface of a photocatalytic surface originates with the formation of electron-electron hole pairs that arise from optical stimulation. Activation at the surface typically has a finite lifetime that is limited by illumination and recombination of electron-electron hole pairs. Mitigation of these effects has been investigated primarily via chemical modification of the titania particles, although there has been no consensus in technical approach for manufacturing practical photocatalyst materials and systems.

Widespread proliferation of new technologies is often highly constrained by financial considerations such as return on investment and the availability of adequate capital.

Currently the general lighting industry (estimated market size over $30B), is undergoing a revolution characterized by both technological and capital investment aspects; adoption of solid state lighting (SSL) is gaining momentum. SSL technology has made enormous strides since the invention of efficient blue LEDs in the 1990's, and completely new vertically integrated supply chains have arisen to address the needs for specialized raw materials, opto-electronic semi-conductors (LEDs and eventually OLEDs), phosphor and packaging materials, manufacturing equipment, interconnects, LED controllers and microcontrollers (MCUs), power supplies, fixturing, luminaires, etc.

The inventors of the innovations described herein believe that technically superior and commercially viable photocatalytic systems may be achieved by leveraging semiconductor technology and the capital investment environment of microelectronics and SSL industries.

SUMMARY OF THE INVENTION

One aspect of the invention relates to fabrication methods to form ultra-thin and highly uniform photocatalytic materials based on titanium dioxide, titanium dioxide doped with rare earth oxides, (e.g. $TiO_2$-$CeO_2$ or any other lanthanide or combination thereof), with transition metals (e.g. Co, W, V, W, Zr, Cu, Fe Cr) or the aforementioned materials combined with metal nanoscale or microscale metal particles at the titania surface, e.g. Pt, Ag, Cu, Fe etc. All of these composite, doped and metal article containing titanium oxide based materials, including but not limited to the stoichiometric $TiO_2$ formulations, will be referred to as "titania" in the description and claims of this invention. Combinations formulated for photocatalytic activity will be referred to as 'photocatalytic titania based materials' in the description and claims of this invention. In this context ultrathin may be defined as the minimum thickness required to exhibit desired photocatalytic surface properties, i.e. typically 3-50 nm. physical thickness. Such ultrathin layers of the subject invention will be particularly useful when formed on optically useful substrates such as those with high optical transmissivity, high reflectivity, and high incoherent reflectivity (e.g. scattering surfaces, either Lambertian or otherwise).

These ultrathin layers may also be particularly useful when formed on high surface area or high porosity open-cell substrates, for example those which have moderate B.E.T. surface area in the range of 5-50 m2/g, or with high BET surface area, e.g. greater than 50 m2/g.

It will be understood to those practiced in the art of photocatalytic materials that the subject invention will also be useful and directly applicable to photo-electrochemical (PEC) cells, super-hydrophilic surfaces, antimicrobial surfaces, self-cleaning surfaces and other related applications of titania-based materials.

Photocatalysis is a surface phenomenon, and therefore the thickness of photocatalytic material may be very small in order to present a suitable chemically activated surface., i.e. in principle less than 10 nm. physical thickness, It evident that such a titania layer must be adequately uniform in order to take full advantage of a high surface area substrate and hence maximize the active area. Microelectronics thin film technologies, especially metal organic vapor deposition (MOCVD) and atomic layer deposition (ALD), are particularly well suited to deposition of thin films of materials.

It is desirable that such photocatalytic films be formed with a high degree of precision in thickness and properties, as well as uniform in thickness across the device and conformal where the substrate has topological surface enhancement. Suitable methods to form films of the subject photocatalytic titania based materials include vacuum sputtering, ion beam deposition, chemical vapor deposition (CVD)/metalorganic chemical vapor deposition (MOCVD), and atomic layer deposition (ALD), in order of increasing inherent uniformity and conformality.

Films of photocatalytic titania based materials may be deposited by vacuum sputtering using metal targets or alloyed metal targets and a reactive oxidizing gas such as oxygen. The process may also employ oxide targets or alloyed oxide targets. In the case of unalloyed targets, the targets may be used simultaneously or in alternating fashion Vacuum sputtering is carried out at reduced pressures, typically in the pressure range of 10-5 Torr. Ion beam deposition is carried out at reduced pressure and results in very smooth films.

These processes are carried out in a chamber capable of producing suitable vacuum pressures and the substrate may be stationary or moved in a linear or other manner, and may be called Physical Vapor Deposition (PVD).

Any of these techniques for thin film deposition may individually and collectively be referred to as "low pressure" deposition techniques in the description and claims of this invention.

Other "in air" deposition techniques can be used to deposit the photocatalytic films herein described, such as, but not limited to, spin coating and heat treating, flame jet deposition, and roll coating. These atmospheric pressure techniques typically have reduced thickness control and conformality capabilities relative to low pressure techniques, but lower costs for manufacturing as well because the atmosphere for the deposition process is not highly controlled, as in the case of low pressure deposition techniques. It is intended that the scope of this invention include both low pressure and "in air" atmospheric pressure deposition techniques for deposition of photocatalytic films.

Deposition of one or more other coatings to modify the optical properties of substrates may also be carried out. These additional coatings, if any, may be deposited in the same chamber or chambers as the photocatalytic thin films are deposited in, or in different chambers. The additional coatings may be deposited by the same techniques as those which are used to deposit the photocatalytic thin films, or may be deposited by different techniques.

CVD, MOCVD and ALD may be carried out with gaseous, solid or liquid precursors, which may be dispensed to the low pressure coating chamber by passing a carrier gas over the source, or dissolved in solvent for liquid delivery to a vaporizer and thence to the vacuum coating chamber. Suitable precursors include halides, amides, amidinates, beta-diketonates, alkoxides, iminates, kitiminates, guanidinates and various Lewis base coordinated molecules. Suitable organic solvents include straight and cycling alkanes, alkenes, and alkynes, alcohols, and aromatic liquids. Deposition may be carried out at atmospheric pressure, in which case the gases used for deposition are typically controlled such as to exclude air, or preferably sub-atmospheric pressures.

The deposition of the film via CVD and MOCVD preferably uses precursors with compatible ligands that do not result in detrimental ligand exchange. Examples of such precursors include $Ce(thd)_4$ and $Ti(OiPr)_2(thd)_2$, $Ce(thd)_3$-L and $Ti(OiPr)_2(thd)_2$, $CeNR_1R_2$, $TiNR_1R_2$, where $R_1$ and $R_2$ comprise H, methyl, ethyl, propyl, etc. For ALD, the aforementioned precursors may be used together in dosing pulses to create an alloyed film, or separate pulses of Ti and the lanthanide may be used to create a layered film. Additional precursors suitable for ALD include Ti(Cp)$_4$ and Ce(Cp)$_4$ along with variously modified cyclopentadienyls where H is substituted by alkyls. Ti(OiPr)$_4$ or other alkoxides may be used, as well as Ti halides, e.g., TiCl$_4$, TiBr$_4$, TiI$_4$.

Additionally, the CVD/MOCVD process may be carried out in a pulsed manner in which the precursors are separated from the co-reactant.

Co-reactants suitable for CVD and MOCVD include oxygen and nitrous oxide. For ALD, oxygen and nitrous oxide may be used, or more reactive species such as plasmas of the oxidizing gas(es), ozone, or water.

The ultrathin characteristic of the subject photocatalytic material has high utility in that the optical function of the substrate/optical element may be predominantly unaffected. In some cases the subject ultrathin material may be incorporated and optimized as the outer layer in that element's optical interference coating design.

A related aspect of the invention are fabrication methods to conformally deposit the subject titania or titania based thin film materials on a substrate that has a high degree of nanoscale or microscale roughness, in order to increase the surface area of the resultant photocatalytic titania based material and to enhance the photocatalytic effect.

A related aspect of the invention describes fabrication methods to form the subject photocatalytic titania based materials with a crystallographic structure that is optimized for efficient photocatalytic activity (e.g. anatase crystal structure) and to therefore enhance the photocatalytic effect.

A related aspect of the invention describes fabrication methods to form the photocatalytic titania based materials with optical absorption shifted to longer wavelengths (e.g. >400 nm.) in order to utilize visible light LEDs to stimulate the photocatalytic effect.

Another aspect of the invention relates to the geometry of the UV or visible light irradiation, such as from the back surface of a substrate, or via waveguide propagation through the substrate that supports the ultrathin photocatalytic titania based material. It is evident that such titania based photocatalytic layers need to be extremely thin and highly uniform in order to allow some fraction the illumination photons to reach and be absorbed near the front surface of the photocatalytic material.

The use of the subject ultrathin catalytic materials on transmissive optical elements open many possibilities for purifier designs in applications where it is constraining, difficult or impossible to use front surface illumination, i.e. to avoid positioning the UV or visible illumination system in the medium to be purified. This configuration may be useful for both gaseous media and liquid media purification.

For purposes of this invention, liquid may refer to any mixtures of liquids, colloids and solids, capable of flowing via gravity or being pumped. Said liquids may contain dissolved gasses or solids. In an exemplary embodiment, said liquid is primarily water. Gas may refer to any mixture of gaseous elements, whether free flowing or pumped. Said gases may include entrained liquid or solid particles. In an exemplary embodiment, said gas is primarily air. For purposes of this invention, flowable media may refer either to gasses or liquids.

The invention includes monolithic integration of a ultrathin titania based photocatalytic material on the surface of a solid state light emitting device such as an LED or OLED. In this context the LED devices may be individually packaged die, multiple die modules, LED lamps (e.g. conventional light bulbs, MR-16s, etc.), lighting fixtures and luminaires. For LED packages and modules, the photocatalytic material would be back surface illuminated in these integrated devices. For LED lamps, fixtures and luminaires, the photocatalytic material may be either from or back surface illuminated, depending on technical and aesthetic aspects of the device design.

Several aspects of LED lamp products and technology may be especially useful to create fluid purification functionality via incorporation of ultrathin photocatalytic materials on an LED die, module or lamp envelope or luminaire transmissive, reflective or scattering surface. For example, LEDs may have white or blue optical output which may be adapted for purposes of this invention as the photocatalytic illumination source.

Integral LED driver ICs Lamps and high power LED modules often incorporate or are packaged with control ICs. In an embodiment of this invention, these control ICs, if present, may be straightforwardly adapted to communicate with and control additional UV LED die and for control algorithms, both being applicable to auxiliary photocatalytic illumination source.

High performance packaged LEDs incorporate physical optics techniques such as surface roughening and texturing, in order to increase optical out-coupling, light output and hence output efficiency. Surfaces of this type, when modified by the addition of an ultrathin photocatalytic material in an embodiment of this invention, will have larger surface area and hence higher purification efficiency.

High performance LED lamps are engineered to remove waste heat, which would otherwise cause the device to operate at high temperatures, thereby reducing device lifetime. Airflow parallel to the lamp surface is optimized to remove heat. This concept of engineered airflow may be adapted in an embodiment of this invention to efficiently exchange air to be purified at a photocatalytic surface. In a preferred embodiment, that photocatalytic surface may be back surface illuminated, i.e. via a transmissive substrate that has high transmissivity at the photocatalytic illumination wavelength.

Another aspect of the invention relates to front surface illumination geometry of the UV or visible light irradiation. The subject ultrathin photocatalyst layer may be formed on a highly reflective surface, such as on a metallic layer, on an all-dielectric interference coating, or on a dielectric enhanced metal reflector, and the photocatalyst-reflector system may be optimized to enhance the photocatalytic effect. Reflector surfaces may be formed either on an opaque metallic, plastic or ceramic material via conventional optical coatings or other treatments, or on a glass or plastic transparent surface, employing similar techniques.

A related aspect of the invention utilizes front surface illumination of a particle, ceramic coated or other preexisting surface that has optical utility, onto which the titania based photocatalytic surface has been formed. That surface may have a high degree of optical scattering, e.g. a highly Lambertian scatterer for the visible, ultraviolet or infrared spectral regions. That particle or ceramic coated surface may also be a remote phosphor used in a blue or UV LED pumped white light luminaire, i.e. a phosphor that is not configured on the LED package material, but at transmissive, reflective or scattering surfaces at distances typically ranging from 1-200 mm from the packaged LED die or LED array.

Several further aspects of the invention incorporate photocatalytic fluid purification systems that utilize the photocatalytic materials and illumination inventions cited above. One such invention relates to purification of surfaces of medical tools, kitchen counter top surfaces, or other implements or everyday items, either during use or when in storage.

Another aspect of the invention relates to air purifier systems that incorporate the inventions cited above. These air purifier systems may be provided as standalone systems, or as systems that are integral to a room or isolated space that requires ambient conditions, walls and other confining surfaces to have a high degree of purity with respect to contaminating chemicals or contagion.

It is evident that such purification systems will maintain extremely low levels of contamination on the surfaces of the system and hence the subject inventions include surface purification systems.

Related aspects of the invention include purification of other flowable media besides air, such as, but not limited to, water, other aqueous liquids including in-vivo fluids, and non-aqueous liquids.

Several related aspects of the invention are methods to enhance the photocatalytic purifying process by increasing the exchange of flowable media at the purifying photocatalytic surface or substrate. In the context of this patent, substrate refers to any object or structure of any shape on which a photocatalytic thin film may be disposed. This substrate may have simple geometric forms, such as a flat plane or simple curves, or may be shaped into more complex geometric forms with higher surface area such as, but not limited to, fins, channels, or tubes. These complex geometric forms may serve several purposes, such as, but not limited to, increasing surface area of the photocatalytic film, improving or controlling flow of the flowable media, and shedding or transferring heat. A surface may be considered a complex geometric form if it has at least 1.5× the surface area of a simple geometric form, such as a plane, a cylinder or a sphere.

Flow of the flowable media to be purified may take place by means such as, but not limited to, convection, gravity, fans or pumping. Flow may take place past structures such as, but not limited to, fins or channels. Flow may also take place through structures such as tubes, which may be regular in shape and form or which may be irregular, such as through a porous media. In a preferred embodiment of this invention, the structure comprises an open celled foam. Flow may be accomplished by active fluid pumping systems, or by passive means, or by a combination of active and passive means. Passive means may increase movement, turbulence and exchange of fluid via convection, resulting from the shape and orientation of the photocatalytic surface, and/or including localized introduction of heat to the fluid. Such heat may be waste heat from the UV or visible photocatalytic illumination source, waste heat from an integral lighting system, or from other sources. Systems including, but not limited to, pumps, directional convection, valves, fans, pressure differences, and gravity may be used to achieve anisotropic flow of the flowable media, that is, flow primarily in a particular direction past the photocatalytic device or film.

A further aspect of the invention relates to photocatalytic air purifier systems that incorporate combined purifier and lighting functions. These combined lighting and photocatalytic purification systems may incorporate either back surface or front surface illumination of the titania based photocatalytic material. Such combined function systems may either be for specialized use, such as, but not limited to, in operating room or other clean room environments, or for general lighting, for example in private residences, schools and workplaces.

The invention includes operational modes for the subject photocatalytic fluid purification systems. In some cases for either back surface or front surface photocatalytic illumination of the photocatalytic surface, such as in the case where UV or visible irradiation is employed, the illumination may be unhealthy or unpleasing for people. In such cases the illumination may be intermittently turned on & off based on daily schedules, detection of people via movement or by electronic ID schemes, or by other means and logical schemes.

In combined purification and lighting systems, the invention includes combination of photocatalytic illumination sources with the spectrally balanced general illumination lighting sources. In one example, for an LED lighting array, white light LEDs may be packaged together with short wavelength LEDs (e.g. blue, violet or ultraviolet emitters) such as InGaN LEDs with emission wavelength less than 450 nm. that have no phosphor. Such short wavelength LEDs in the array may be controlled separately as described above or as based on other logical schemes.

The present invention may include a number of the inventive elements summarized above, in a variety of combinations and configurations.

The Inventions summarized above are illustrated in several examples.

DETAILED DESCRIPTION OF THE INVENTION, AND PREFERRED EMBODIMENTS THEREOF

Figure 1:
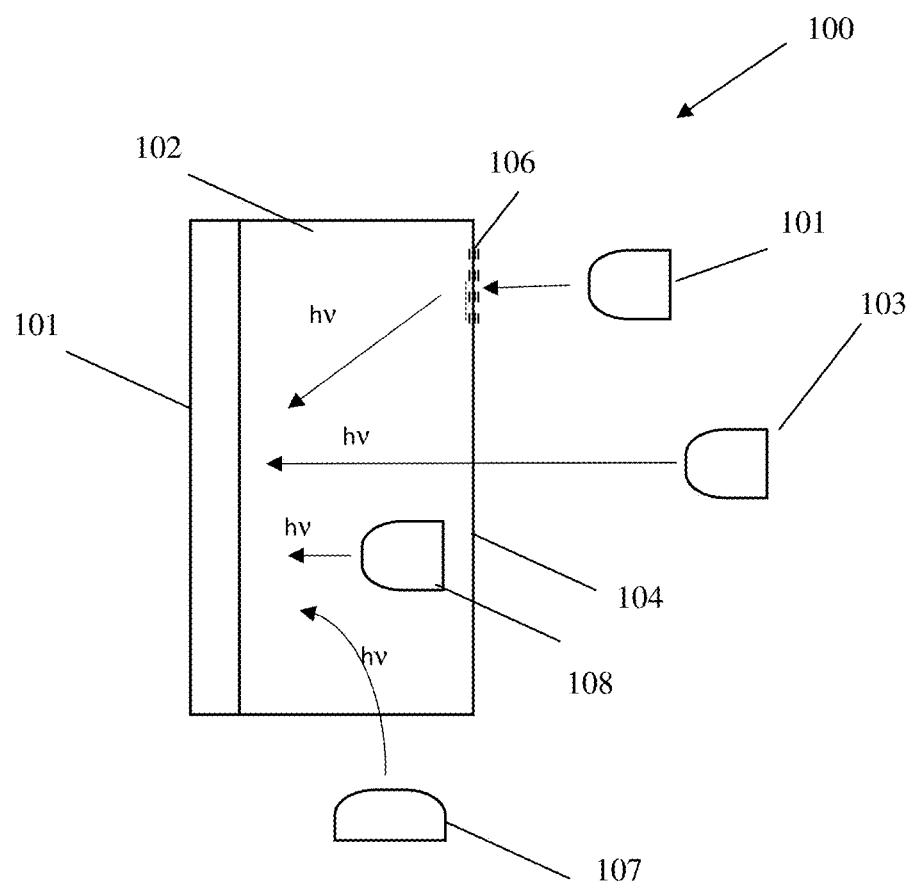
FIG. 1 is a schematic of a back surface illuminated photocatalytic device, illustrating various geometries to couple the light source configurations.

The present invention relates to novel photocatalytic materials, fabrication methods for those materials, and novel photocatalytic devices and systems. The invention also describes an apparatus and associated methods of construction and operation for combining a photocatalytic thin film with a light source in order to purify a flowable media. Particular embodiments will focus on LED light sources and use in air, but any of the embodiment disclosed herein may be combined in any fashion in order to carry out the purposes disclosed herein.

In one aspect, the invention relates to the use of vapor phase or low pressure methods to deposit a uniform layer of titanium dioxide film, a mixed titanium oxide lanthanide oxide film, or a mixed film with metal particles incorporated on our near the surface. Lanthanides include La, Ce, Pr, Nd, Pm, Sm, Eu, Gd, Tb, Dy, Ho, Er, Tm Yb, and Lu. These methods include, by way of example, sputtering, evaporation, metalorganic chemical vapor deposition (MOCVD), and atomic layer deposition (ALD), and they typically take place in a chamber at pressures below atmospheric pressure and with a controlled atmosphere.

Evaporation is the simplest method and co-evaporation of oxide sources may be used to deposit a uniform substantially homogeneous film over a planar substrate. Alternatively, elemental sources may be used in an oxidizing environment. Sputtering from a uniform or composite target may also be used on planar surfaces and to some degree on curved surfaces.

MOCVD has the ability to form a uniform layer on curved surfaces and surfaces with complex geometry that have a high degree of topography. In the case of MOCVD, the deposition temperature is kept in a range where conformality is high and the deposited film is substantially amorphous. In one embodiment, a photocatalytic film, ceria doped titania, is deposited by MOCVD. The precursors, $Ce(thd)_4$ and $Ti(OiPr)_2(thd)_2$ are dissolved in an organic solvent and delivered to a vaporizer in maintained at a temperature in the range of 150-250° C. Argon carrier gas is flowed through the vaporizer at 100-200 sccm and into a deposition chamber where the substrate is held at a temperature of 450-650° C. and a pressure between 1 and 20 Torr. Oxygen is flowed as a co-reactant gas at between 400 and 1000 sccm. A thin ceria doped titania film is deposited on the substrate. The thickness of the ceria doped titania film may be between 1 and 30 nm.

Atomic layer epitaxy (ALD) may be used to deposit uniform layers onto the aforementioned surfaces and also on highly curved surfaces or into features of very high aspect ratio (e.g., >3:1). In one embodiment the photocatalytic film is deposited by ALD. The precursors, $Ce(Cp)_3$ and $Ti(Cp)_4$ are transported together by argon carrier gas flowed at 100-200 sccm and into a deposition chamber where the substrate is held at a temperature of 150-450° C. and a pressure between 1 and 20 Torr. The combined $Ce(Cp)_3$ and $Ti(Cp)_4$ gas phase precursor is delivered for a specific time, followed by an inert gas purge, then oxygen is flowed through a water bubbler held at between 5-15° C. as a reactant gas, followed by an inert purge. Reactant and inert gas purge flows are between 200-1000 sccm. This set of pulses is repeated until a thin ceria doped titania film is deposited on the substrate. In a preferred embodiment of this invention, the ability of ALD to deposit layers on extremely high aspect ratio structures may be used to form a photocatalytic thin film on an interconnected porous structure such as, but not limited to, that of an open celled foam.

In another embodiment, the ALD process employs separate pulse trains of $Ce(Cp)_3$ and $Ti(Cp)_4$ precursor, each followed by the oxidizing and purge steps as described above. Composition of the resulting titania-lathanide material would in those cases be determined by the ratio of $Ce(Cp)_3$ and $Ti(Cp)_4$ ALD cycles.

MOCVD may be carried out with solid sources held in bubblers through which a carrier gas is flowed to convey the source to the deposition chamber. The sources may also be dissolved in an organic solvent as individual sources or combined together. Key criteria of a solvent system are (1) high boiling point to reduce the chance of flash off of the solvent, (2) high solubility for the compound, (3) low cost. Useful hydrocarbon solvents may include, for example: octane, decane, isopropanol, cyclohexane, tetrahydrofuran, and butyl acetate or mixtures comprising these and other organic solvents. Lewis base adducts may also be incorporated as additions to the solvent(s) for beneficial effects on solubility and to prevent possible oligimerization of the precursor molecules. Examples of useful Lewis Bases include polyamines polyethers, crown ethers, and the like. Pentamethylenediamine is a one example of a polyamine. Examples of polyethers include various glymes such as mono-, di-, tri-, and tetraglyme.

Most MOCVD processes have two temperature regions of interest: a surface reaction kinetic limited range at lower temperature and a mass transport limited range at higher temperature. Co-reactants useful for forming high quality mixed ceria-titania films include oxygen and nitrous oxide. In general, there is a large excess of oxygen in the process, so that carbon incorporation in the film is minimized. The primary objective in the present invention is the formation of a film of as homogenous a nature as possible, preferably a film of substantially anatase crystal structure.

Depending on the substrate and titania-lanthanide film composition, seed layers or other thickness dependent inhomogeneities may be utilized to enhance formation of the anatase phase, optimize absorption of the photocatalytic illumination, increase surface hardness or durability, or to otherwise enhance the photocatalytic effect. In this context seed layers may be introduced as part of an ALD, MOCVD or PVD process, or via an different process.

In some embodiments, lateral composition, topographic or microstructural inhomogeneities may be engineered in the surface, in order to achieve specific hydrophilic or hydrophobic properties in order to modify fluid flow characteristics at that surface.

The deposition system may have an automated throttle valve that allows pressure to be controlled independently of flow. In this way, residence times can be manipulated more directly. The hot-wall type reactor is one type of reactor that may be used to deposit the subject films. Alternatives include batch hot-wall reactor or warm-wall showerhead type reactors.

Useful MOVCD process conditions span a range of temperature from 250° C.-650° C. and total pressure between 0.5-50 Torr. Preferably, the process temperature is below 500° C., and pressure is between 1 and 10 Torr.

The use of ALD to create a crystalline mixed titania-ceria film affords a higher degree of conformality than MOCVD. ALD also offers the possibility of batch processing. ALD is a surface saturation limited method for depositing thin films in which alternating pulses of reactants are introduced to the process, generally separated by an inert purge pulse. Typically, one reactant contains the cation and a second reactant contains the anion (oxygen in this case). The advantage of ALD is that each layer formed by a surface saturation limited cation containing layer, that is subsequently purified and/or oxidized by the second reactant pulse. A typical ALD cycle consists of the first reactant pulse, a purge pulse, the second reactant pulse and another purge pulse. The cation containing layer may be formed using any suitably volatile precursor, e.g., a metalorganic, a metal halide, metal hydride, or combinations thereof.

Forming a composite or multicomponent oxide film by ALD may be accomplished using different approaches. In the first approach, the substrate is exposed to two or more metal cations simultaneously. The ratio of cations in the precursor (reactant) is chosen to achieve the desired ratio of cations in the film.

In the second approach, the cations may be alternated by ALD cycle. The desired composition is achieved by choosing the ratio of one cation cycle to the other. As an example, for a 25% alloy of species B in oxide A, 1 cycle of species B would be followed by 3 cycles of species A.

Similar precursors to the MOCVD process may be employed for ALD. Cyclopentadienyl coordinated metal precursors may also be advantageously used for ALD of ceria-titania films. For the case of simultaneous introduction of the metal containing precursors, source materials are chosen so that there is compatibility between the chemistries such that unwanted ligand exchange is prevented. Process conditions favorable for ALD are in the temperature range of 100-375° C. with pressures in the range of 1-5 Torr. Co-reactants (oxidizers) include oxygen, nitrous oxide, plasmas of these gases, ozone, or water. We note that surface preparation (termination) can be very important in ALD. Pre-treatments to promote uniform nucleation include aqueous acids/bases compatible with the substrate and that result in —H or —OH termination of the substrate surface.

Anion doping of the titania film may also be employed in the films of the subject invention e.g., incorporation of nitrogen via either ALD or MOCVD. This may be accomplished by using a nitrogen containing co-reactant, e.g. ammonia or other amines, nitrogen oxides, plasmas or combinations of these, with or without oxidizing reactants.

Other materials may be incorporated below, above, or in the oxide film. An example is a metal that substantially maintains its metallic character that may act in an optically or photocatalytically enhancing manner. The metal may be deposited by any suitable means, including evaporation, sputtering, chemical vapor deposition, or ALD. They may be deposited on the substrate before film deposition takes place, during film deposition, or after film deposition, or in any combination thereof. Noble or precious metals that strongly segregate from the alloyed oxide may be used, for example Pt or Ag. These could be incorporated into the oxide ALD process or separately using the aforementioned methods. Non-strongly segregating metals may also be used, provided that the processing temperatures of the oxide film deposition method do not cause the metal to incorporate into the oxide such that it loses its metallic character. Optionally, thermal treatments such as annealing may be used to promote agglomeration of the metal or de-wetting to form island structures.

Metallic particles may be dispersed onto the film by depositing the metal by physical vapor deposition means such as, but not limited to, evaporation or sputtering. The metallic particles may include transition, precious, or noble metals. For example, Pt may be deposited by vapor phase means. In the case of evaporation, the metal may be deposited by resistive heating of a charge or by electron beam heating at reduced pressure. Preferable reduced pressures are below 10-3 Torr. Sputtering of Pt may be carried out at reduced pressure. In either evaporation or sputtering, the metal may be deposited on the Ti-lanthanide film at room temperature or at elevated temperature. The film is heat treated to induce de-wetting to form small islands. This is preferably performed in a oxidizing ambient, the temperature and degree of oxidizing atmosphere chosen to be compatible with the substrate upon which the titania film has been deposited. The island size defining the lateral dimensions of the metal particles may be between 200 nm and 1500 nm is preferably between 5 and 50

Doping of the photocatalytic titania based materials with metallic species segregated on an atomic scale, such as Ag, Au, Cu, Pt and Fe, may also be accomplished using the aforementioned techniques.

Incorporation of metal particles in such titania based photocatalytic materials may serve three separate and functionally complementary functions:

1) Enhancement of optical absorption. Ag is of particular interest because of the surface plasmon resonances on the near UV-blue spectral regions
2) Retardation of recombination of photocatalytic illumination generated electrons and electron holes, especially Pt and platinum group metals. This is a well known effect in particle based catalyst systems.
3) Complementary antimicrobial effects of metals that are highly electronegative, especially Cu and Ag.

The present invention may utilize one or several species or size scales of metal particles incorporated in a thin film titania or doped titania or composite titania thin film matrix, to achieve one or more of these three phenomena depending on the desired purpose or application. ALD of composite materials of this type are of particular interest based on the capability of that technique to form precise nano-laminates of dielectric and metal composite structures.

Other aspects of the subject invention include geometric and physical optics schemes to exploit the surface chemistry and hence purification attributes of ultrathin titania based photocatalytic materials as described above. We note that the principles described below may also be utilized with previously identified photocatalytic materials, both those based on titanium dioxide and also based on other materials.

The photocatalytic materials of the present invention, such as those described above, and others that include, may be deposited on various substrates and in a variety of configurations also identified in the present invention, thereby enabling a range of photocatalytic fluid purification devices. Photocatalytic purification may be used to remove organic and other chemical species from a fluid that may be either gaseous (e.g. air) or liquid (e.g. water). Impurity species in such a fluid are brought into near proximity or adsorbed at the photocatalytic surface, and are subsequently chemically dissociated.

In general gaseous fluids to be purified by such devices include ambient air in residential, commercial, industrial and public building environments, as well as specialized application environments that include manufacturing clean rooms, hospital operating and recovery rooms, etc. Liquid fluids to be purified include drinking water as well as in-vivo and in-vitro purification and chemical processing in medical and biomedical applications.

In general, a photocatalytic fluid purification system requires three conditions:
  I) a photocatalytic surface
  II) a source of radiation to excite the photocatalytic effect ("photocatalytic illumination")
  III) a fluid exchange means to move fluid across the surface of the photocatalytic material.

The photocatalytic surface may be a solid substrate that has had one or more surfaces modified to incorporate photocatalytic material. Depending on the application, the fluid meant for purification, the surface area necessary for efficient purification, the geometry and wavelengths of the incident photocatalytic illumination, a variety of substrates may be employed.

The fluid exchange means III is comprised of mechanical confinement to channel the fluid exchange flow, and a way to drive that flow.

For titanium dioxide photocatalytic materials, and for some embodiments of the present titania based photocatalytic materials, photocatalytic illumination is necessarily in the 200-400 nm. spectral region. For titania-lanthanide and titania-transition and metal particle or metal doped materials of the present invention, photocatalytic illumination may be in the 400-450 nm. spectral region.

For some fluid purification applications, either gaseous or liquid purification, the photocatalytic material and fabrication of that material may be advantageously utilized on substrates of various shapes and surface finishes that facilitate conditions II and/or III in the preceding paragraph.

Combined Lighting and Purifications Functions

There are a range of embodiments for the present invention that incorporate combined lighting and air purification functions. In those applications and configurations certain attributes of the lighting system may be advantageously adapted to provide either Condition II and/or Condition III as described above.

These combined lighting and purification functions may be enabled by fabricating a photocatalytic material on surfaces that have optical utility for the lighting device, as a partial or comprehensive way to satisfy Condition II. These "optically useful surfaces" may be either specularly reflective, specularly transmissive, non specular, (i.e. scattering) transmissive or reflective surfaces, the surface of an up-wavelength converting phosphor (i.e. Stokes shifting), or combinations of these optical surface types, which are incorporated in the lighting device. In such cases in which the photocatalytic material is applied to an optically useful surface, such material may be the titania based material of the present invention, or another photocatalytic material that is known to in the art.

One potentially useful attribute of a lighting device or light source is its optical output ("lighting illumination"), which is typically broadband in the 400-700 nm ("visible spectrum") spectral region. Whereas incandescent, metal halide and fluorescent light sources tend to emit lighting illumination that is somewhat broadband over the visible spectrum, light emitting diodes ("LED") used in lighting often have a strong blue or violet spectral emission.

Although the majority of the discussion below addresses adaptations and use of LED light sources, we emphasize that any light source may in principle be utilized if it offers suitable short wavelength output, or has other attributes as described below.

White light emitting LEDs typically employ either one of two white light generating mechanisms. The most common mechanism uses a blue/violet LED that excites a phosphor; the resulting lighting illumination is comprised of the original blue/violet light, mixed with longer wavelengths in the green, orange and red portions of the visible spectrum.

The second, less common white light generating mechanism employs three LEDs, typically red, green and blue (RGB). In these cases the emission of these RGB spectral components are mixed to generate white light, and in some LED devices the spectral irradiancy of each RGB component may be controlled by a microcontroller, e.g. using pulse width modulation, in order to generate a continuum of white light color temperatures or different colored light entirely.

For either of these two white light generating LED mechanisms, the short wavelength components of LED lighting illumination will typically be in the 400-470 nm. spectral region. In the former of the two mechanisms, the short wavelength phosphor pump wavelength may also be in the ultraviolet, with wavelength in the 300-400 nm spectral range. In general, LED light sources that have stronger relative output in the 360-420 nm spectral range may offer greater utility and flexibility to incorporate the inventive concepts herein.

In some embodiments of the present invention, certain short wavelength spectral components of the lighting illumination may usefully also serve as the photocatalytic illumination. Although LED lighting devices are particularly well suited to provide such short wavelength photocatalytic illumination, we note that other lighting illumination sources may also be utilized in the subject invention.

Combined lighting and purification systems that utilize spectral components of the lighting illumination to serve as the photocatalytic illumination source, without the use of auxiliary photocatalytic illumination sources, will be denoted as "Mode 1".

In related and complimentary embodiments, the photocatalytic illumination may be completely provided by an auxiliary photocatalytic illumination source, and the lighting and purification functions would in those cases share other attributes of the combined system such as optically reflective, transmissive, scattering surfaces, and fluid flow controlling surfaces. The lighting illumination may also be usefully combined with an auxiliary photocatalytic illumination source, in order to increase the sum total of the photocatalytic illumination. Combined lighting and purification systems that incorporate an auxiliary photocatalytic illumination source will be denoted as "Mode 2".

Other embodiments of combined lighting and purification systems may advantageously employ certain heat dissipation and fluid dynamics/confinement attributes of select lighting device as a means to completely or partially satisfy the photocatalytic purification Condition III as described above.

In general, all electrical powered light sources are inefficient to some extent, in that significant electrical input power is not converted into visible light (lighting illumination), but is instead converted to thermal energy that heats the light source. This is especially true for tungsten-halogen lamps, incandescent lamps, ceramic metal halide sources and solid state light (SSL) sources such as LEDs and organic LEDs (OLEDs). Higher temperature operation is typically not a major issue for all of these except SSL sources, since increases in the source temperature shift the predominant blackbody radiation to shorter wavelengths, thus increasing the visible light output to some extent. On the other hand, SSL sources such as LEDs are deleteriously affected by operation at high temperature; device lifetimes are dramatically reduced. Therefore, LED lighting devices, especially high brightness LEDs (HB-LEDs), are designed and configured with intrinsic cooling features. Typically the LED packaged die is attached to a heat sink base in a high thermal conductivity structure, and the base is in turn attached to cooling fins and/or a large thermal capacity structure that can dissipate the heat. Certain LED light sources, especially LED lamps and LED luminaires, employ fairly sophisticated designs to remove the LED waste heat using convective flow.

One embodiment of the subject combined lighting and photocatalytic purification systems is to take advantage of the waste heat and to harness the resultant convective flow across both optically useful and convective flow confining surfaces in lighting devices, especially for LED lamps and luminaires. There are a wide variety of convective cooling/air exchange schemes that may be established in concert with optical surfaces configurations, and several such designs are provided in the Embodiments. These embodiments are in no way limiting as to how the inventive design principles may be utilized in these types of devices and systems.

Convective flow across heated surfaces in such devices may in some cases be augmented with mechanically driven flow such as from an electrical blower, or in some cases the waste heat may be predominantly driven be auxiliary blower systems. The exhaust for LED lamps and luminaires, which will be made up of partially purified input air, may directly enter the upper regions of that room, may be recycled and reintroduced to the photocatalytic surface, or in the case of recessed ceiling lighting, it may be delivered back to that room or another space by a duct, or system of ducts. Such ductwork may transport the purified air either from one of the subject devices, or from a system of many devices, as in a room with multiple ceiling recessed luminaires, for example.

We note that although the discussion is primarily using LED light sources as an example, many other light source types may be used to take advantage of these inventive principles. In particular, fluorescent light sources are well suited to take advantage of this invention, as they may be designed to emit short wavelengths of light which may be useful to stimulate the photocatalytic effect. As with the LED embodiments, photocatalytic thin films may be directly integrated with the light emitting object, or may be present on a reflector or on a transparent or translucent diffuser sheet near the light emitting object. Such a reflector or diffuser sheet may, regardless of the light source, be designed for insertion into a system having a light source, without replacement of the entire light fixture or luminaire.

Many LED lighting devices that may be utilized to affect the combined lighting and purification functions described above. These LED lighting devices include Packaged LEDs, LED Arrays, LED lamps and LED Luminaires. Each of these types of LED lighting devices may employ the subject inventions in specific ways as appropriate to address specific applications and product markets. Some possible embodiments to utilize these LED light sources in fluid purification functions are described in the attached Table.

LED Light Sources and Configurations for Combined Lighting-photocatalytic Utility Three criteria for photocatalytic fluid purification are:
a photocatalytic surface
a source of radiation to excite the photocatalytic effect ("photocatalytic illumination")
a fluid exchange means to move fluid across the surface of the photocatalytic material.

Two Modes to provide Photocatalytic Illumination in a combined Lighting/Photocatalytic purification system are:
Mode 1
Combined lighting and purification systems that utilize spectral components of the lighting illumination to serve as the photocatalytic illumination source, without the use of auxiliary photocatalytic illumination sources.
Mode 2
Combined lighting and purification systems that incorporate an auxiliary photocatalytic illumination source that provides either all or a fraction of the photocatalytic illumination. In the case of that auxiliary source providing a fraction, the balance of the photocatalytic illumination would be provided by violet or blue spectral components of the lighting illumination.

TABLE 1

| LED light source type | Light source description | Light source application for photocatalytic purification | Photocatalytic purification criteria | | |
|---|---|---|---|---|---|
| | | | Condition I: Photocatalytic material | Condition II: Photocatalytic illumination | Condition II: Fluid exchange means |
| Packaged blue or violet LED | Single LED die (emission wavelength 400-450 nm.) in a conventional package. | Packaged LED is incorporated in a fluid flow-purification system, preferably liquid, due to the relatively small area of packaged LED. | Photocatalytic material formed on outer surface of transparent package substrate. Material is titania-based and optically absorbing at LED emission wavelength. | Mode 1 Light source directly excites back surface of photocatalytic material (substrate side), via transmission through substrate. | Extrinsic to light source. One embodiment is a liquid flow component made from fused silica or other materials that transmit the photocatalytic illumination, with the interior surfaces of the flow passages coated with an ultrathin titania based photocatalytic material. The blue/violet or UV light source is coupled into a solid portion of the silica flow element and this photocatalytic illumination is confined within the element via waveguiding and/or reflective means. A related embodiment is a |
| Packaged UV LED | Single UV LED die (emission wavelength 200-400 nm.) in a conventional package. | Packaged LED is incorporated in a fluid flow-purification system, preferably liquid, due to the relatively small area of packaged LED. | Photocatalytic material formed or deposited on outer surface of UV transparent silica glass cover plate or dome. Material is titania-based and optically absorbing at LED emission wavelength. | Mode 1 Light source directly excites back surface of photocatalytic material (substrate side), via transmission through substrate. | |

TABLE 1-continued

| LED light source type | Light source description | Light source application for photocatalytic purification | Photocatalytic purification criteria | | |
|---|---|---|---|---|---|
| | | | Condition I: Photocatalytic material | Condition II: Photocatalytic illumination | Condition II: Fluid exchange means |
| | | | | | silica based microfluidic waveguide structure, with blue/violet or UV LED radiation coupled into the silica and propagated via waveguiding and reflective structures to the substrate side of the photocatalytic material deposited in the microfluidic flow channels. |
| Packaged White LED [Blue-violet LED/Phosphor] | A blue or violet or near ultraviolet LED die mounted in a suitably transparent package such as epoxy or silicone. A wavelength down-converting phosphor is typically impregnated or otherwise incorporated in the transparent epoxy. | Blue-violet/phosphor White packaged LED is incorporated in a combined lighting & fluid flow-purification system. | Photocatalytic material formed on outer surface of transparent package substrate. Material is titania-based and optically absorbing at LED emission wavelength. | Mode 1 Light source directly excites back surface of photocatalytic material (substrate side), via transmission through substrate. | Extrinsic to light source |
| White LED array [Blue-violet LED/Phosphor] | An integral assembly of multiple blue-violet LED die in a single package, or multiple packaged LEDs, mounted on a board, a flexible membrane or some other integrating mechanical support, e.g. chip-on board (COB). LED arrays may integrated, typically on a board, with electrical driver, circuitry, and in some cases microcontroller or ASIC dimming and color control, optics and other system components. LED modules that produce white light may be either Blue-violet LED/phosphor or RGB. Alternatively these functions may be provided on a separate board and incorporated with the array in a lamp or luminaire. | Blue-violet/phosphor White LED array is incorporated in a combined lighting & fluid flow-purification system. | Photocatalytic material formed on outer surface of transparent package substrate. Material is titania-based and optically absorbing at LED emission wavelength. | Mode 1 Light source directly excites back surface of photocatalytic material (substrate side), via transmission through transparent substrate. Alternatively, the blue or preferably violet spectral components of the lighting illumination may be incident on photocatalytic surfaces on a lamp or luminaire. | Extrinsic to light source |

TABLE 1-continued

| LED light source type | Light source description | Light source application for photocatalytic purification | Photocatalytic purification criteria | | |
|---|---|---|---|---|---|
| | | | Condition I: Photocatalytic material | Condition II: Photocatalytic illumination | Condition II: Fluid exchange means |
| White LED array [Blue-violet LED/Phosphor] | An integral assembly of multiple blue-violet LED die in a single package, or multiple packaged LEDs, with photocatalytic illumination producing UV LEDs also incorporated in the array. The UV LEDs may be in the UV-A (315-400 nm wavelength), UV-B (280-315 nm) or UV-C (100-280 nm) spectral ranges as appropriate to efficiently produce the photocatalytic effect. | Blue-violet/phosphor White LED array is incorporated in a combined lighting & fluid flow-purification system. | Photocatalytic material formed on outer surface of transparent package substrate. Material is titania-based and optically absorbing at LED emission wavelength. | Mode 2 UV LEDs are incorporated as some fraction of the blue-violet LED array, and are separately powered and controlled, with the UV photocatalytic illumination incident on the back surface of the photocatalytic material (substrate side), via transmission through transparent substrate. Alternatively, the UV illumination may be incident on photocatalytic surfaces on a lamp envelope or in a luminaire, as below. | Extrinsic to light source |
| White LED array [RGB] | An integral assembly of red, blue and green LED die in a single package, or multiple packaged LEDs, mounted on a board, a flexible membrane or some other integrating mechanical support, e.g. chip-on board (COB). | RGB LED array is incorporated in a combined lighting & fluid flow-purification system. | Photocatalytic material formed on outer surface of transparent package substrate. Material is titania-based and optically absorbing at LED emission wavelength. | Mode 1 Blue or violet emitting LEDs in the array are preferentially powered and are incident on the back surface of photocatalytic material (substrate side) which has been deposited on the epoxy package, via transmission through that transparent substrate. Alternatively, the blue or preferably violet spectral components of the lighting illumination may be incident on photocatalytic surfaces on a lamp or luminaire. | Extrinsic to light source |
| White LED array [RGB] | An integral assembly of multiple LED die in a single package, or multiple packaged LEDs, mounted on a board, a flexible membrane or some other integrating mechanical support, e.g. chip-on board (COB). | RGB LED array is incorporated in a combined lighting & fluid flow-purification system. | Photocatalytic material formed on outer surface of transparent package substrate. Material is titania-based and optically absorbing at LED emission wavelength. | Mode 2 UV LEDs are incorporated with the RGB LED array, and are separately powered and controlled. The UV photocatalytic illumination incident on the back surface of the photocatalytic material (substrate side), via transmission | Extrinsic to light source |

TABLE 1-continued

| LED light source type | Light source description | Light source application for photocatalytic purification | Photocatalytic purification criteria ||| 
|---|---|---|---|---|---|
| | | | Condition I: Photocatalytic material | Condition II: Photocatalytic illumination | Condition II: Fluid exchange means |
| | | | | through transparent substrate. Alternatively, said UV illumination may be incident on photocatalytic surfaces on a lamp or luminaire. | |
| LED lamp | An integrated & completely self-contained LED light source, often referred to as a light bulb, MR-16, PAR, etc. It is comprised of a packaged LED or LED array, and electrical power circuitry for voltage conversion, rectification and constant current generation. These functions may also be integrally provided as an LED module (as above). The lamp is also comprised of enclosing mechanical structure(s) & optical element(s) to scatter, reflect or transmit the lighting illumination | Combined lighting & fluid flow-purification system. | Photocatalytic material formed on outer surface of lamp envelope, on luminaire reflective, transmissive or scattering surfaces or on a user configurable retrofit optical or mechanical element. In general the thickness of the photocatalytic material on optically useful surfaces, (especially transmissive or metallic reflectors in the lamp or luminaire) is on the order of 10 nm., i.e. < $\lambda/20$ optical thickness for most of the visible spectrum, in order to have a negligible effect on intended optical properties of that surface. When formed on the surface of a dielectric enhanced metal reflector or an all dielectric reflector, the subject titania based photocatalytic material may be incorporated into the interference coating design and the reflector's optical properties and color appearance may be optimized with the incorporated ultrathin titania material, based on standard thin film design techniques. | Mode 1 or Mode 2 Blue violet or UV spectral components generated by LEDs or arrays, as above, are incident on the lamp envelope or onto retrofitted optical and/or fluid flow constraining mechanical elements. For Mode 2, i.e. for cases where UV auxiliary photocatalytic illumination is used, borosilicate glass, plastic or other UV absorbing elements may be employed to prevent UV from escaping to the local environment, and to prevent that threat to people or the environment. Alternatively these UV LED elements may have scheduled on-cycles and/or brief duration in order to achieve the same result. | Fluid flow across the surface of a lamp or a nearby optically transmissive flow confining surface (e.g. a transparent or scattering transmissive flue or configurable globe, may be achieved by convection, and the design of that element may be optimized for maximum fluid exchange and turbulence at the surface of the photocatalytic surface. |
| LED luminaire | A complete lighting assembly/system, (e.g. recessed 1' × 4' or 2' × 4' ceiling or wall panels, recessed lighting, track lighting, floor lamps or table lamps, operating room lighting fixtures, etc.) utilizing one or more LED arrays and/or LED lamps & lamp fixturing, transmissive, reflective or scattering optical elements, mechanical fixturing, and electrical power and controls interface. | Combined lighting & fluid flow-purification system. | | | For luminaires, fluid flow may be similarly optimized across the photocatalytic surfaces on reflective, transmissive or scattering surfaces, and driven by either purely convective forces, or an external blower, either locally at the luminaire, or centrally for an assembly of luminaires, or by a combination of these. |

Surface Purifications Functions

In general, a photocatalytic surface purification system requires two conditions:
 I) a photocatalytic surface
 II) a source of radiation to excite the photocatalytic effect ("photocatalytic illumination")

Healthcare Associated Infections (HAI) are a major problem that threatens life and increases costs of healthcare. The CDC estimates that in the U.S. there are 1.7 million hospital-associated infections annually, contributing to 99,000 deaths. One primary transmission mode for these infections involves contact with contaminated surfaces, where bacteria and viruses can reside for days or even weeks on touch surfaces near the patient. MRSA, C. *Difficile*, MDRA and *Staphylococcus* are particularly dangerous and stubborn contagions that may reside on surfaces close to a patient. Many types are difficult to attack with antibiotics, and antibiotic resistance is spreading to Gram-negative bacteria that can infect people outside the hospital.

Outside the healthcare world, there are a similar and increasing range of opportunistic mass-infections as evidenced by recent Norovirus outbreaks on cruise ships. These outbreaks may be spread by viruses, bacteria and spores that propagate both airborne and from surfaces to surface.

It is well known that many standard disinfecting regimens (typically liquids comprised of bleach or hydrogen peroxide) may leave a residual contagion on a surface, which is known as "Bioburden". Bioburden is comprised of biofilm or planktonic species residing at a surface that is nominally 'clean'. Its presence may be due to failure of hospital staff to follow standard procedures, species with exceptional physical, chemical and biological robustness, or a combination of those. There are several disinfectant treatments that are receiving wide attention as ways to augment liquid treatments. UV-C radiation, ozone and disinfectant vapors or mists are known to be very effective, but are highly hazardous and are only viable when a hospital room has been vacated.

Antimicrobial, or 'self sterilizing' surfaces are highly desirable to complement standard cleaning. They act continuously, and ideally they should have a high killing efficiency for a broad range of bacteria, viruses and spores, and be non-toxic to humans. Silver and copper containing surfaces are the most widely investigated, but these have shortcomings including toxicity, cost and questions about long term efficacy, due to adaptation of bacteria.

The ultrathin titania photocatalytic materials and illumination schemes of the subject invention may be incorporated in a wide range of devices in order to effect or enhance antimicrobial characteristics of surfaces. These materials may be directly applied to solid surfaces of interest, or applied to flexible polymeric materials that are subsequently applied to surfaces or formed into those products directly.

In one embodiment, these products may be incorporated in "high touch" surfaces, surfaces which have a great deal of contact by humans. Examples of these products include, but are not limited to: personal or commercial devices, such as cell phones and smartphones, tablet and computer touchscreens and keyboards, hospital objects, such as bed hand rails over-bed tables, doorknobs, elevator buttons, escalator or stair rails, writing implements, medical tables, instrument panels, and protective face masks, and in-vivo devices including but not limited to joint implants, cardiac pacemakers and defibrillators, catheters or neurological electro-stimulation devices and medical systems such as dialysis equipment.

It is evident that these materials, when incorporated on consumer, commercial and medical products, will be exposed to considerable abrasion, mechanical impact and chemical agents used to clean and sanitize these products on a daily basis.

One advantage of ALD in the subject invention is its capability to engineer composite materials. In the case of photocatalytic titania those concepts were described above. Composite oxides of these types may be formed either by co-deposition during a cation ALD deposition step or via nano-laminates.

One other aspect of the subject invention is to further compositionally modify the titania photocatalytic materials so as to increase the mechanical hardness and chemical resistance of the surface. This may be accomplished via ALD formation of nano-laminates that combine titania with $Al_2O_3$, $SiO_2$, $ZrO_2$, yttria stabilized zirconia (YSZ), or other oxides that have desirable characteristics. In terms of hardness, titania is approximately 5.5-6.5 on the MHS hardness scale, while $Al_2O_3$ is 9. Incorporation if intermittent $Al_2O_3$ ALD steps during ALD of the subject titania photocatalytic materials, will increase the hardness and abrasion resistance of the antimicrobial or fluid purification active surface.

In those cases $Al_2O_3$ may be formed, for example, using an ALD process that is well known to those practiced in this field, for example using trimethylaluminum deposition with vapor phase water as the oxidizing co-reactant.

The present invention and some of its various embodiments are described below, with reference to figures as necessary. Reference numbers are used to match particular elements described in the text with those shown in figures.

One embodiment is shown schematically in FIG. 1. This device 100 is designed to purify the air or other flowable medium at photocatalytic thin film surface 101 by oxidizing reactions with chemical and biological contaminants. A transparent substrate 102 supports a thin film of the subject photocatalytic titania based material 101 on a front surface of substrate 102. In any embodiment of this invention, this photocatalytic thin film 101 may be on the substrate 102 and thereby in direct contact with the substrate 102, or may be over the substrate 102, having one or more intervening layers (not shown) disposed between the photocatalytic thin film 101 and the substrate 102. In a preferred embodiment the photocatalytic material is a solid solution of $TiO_2$-$CeO_2$ (90%/10%). The material has the anatase crystal structure.

The layer 101 is illuminated from its back surface, i.e. from the direction of the substrate side 102 of the material. This back surface illumination may be accomplished using blue emitting LED sources, such as those fabricated using the InGaN material system, with suitable emission wavelengths that induce the photocatalytic effect. In a preferred embodiment this wavelength may be approximately 420 nm. Other types of light sources and emission wavelength ranges may also be used and are also the subject of the invention.

The back surface illumination may be through the thickness of the transparent substrate, with illumination source 103, the emitted light shown with the arrow and "hv" label. In a preferred embodiment the back surfaced illumination may be near normal incidence. In that case the back substrate surface may be coated with an antireflection coating on surface 104 to increase the illumination intensity incident on the photocatalyst.

Back surface illumination may also be achieved by transmitting the illumination from source 105, into guiding modes in the transparent substrate, via coupling structures such as a surface relief grating 106. Alternatively, illumination via guiding modes may be accomplished by illumination of the substrate edges from source 107. Alternatively, the light source 108 may be embedded in the transparent substrate. These techniques may be used to substantially confine the optical radiation to the interior of photocatalytic film 101.

The thickness of the layer 101 is sufficiently thin, e.g. in the range of 10-100 nm., for the illuminating wavelength to be optically absorbed throughout the thickness of the photocatalyst including in the proximity of the outer surface. In that case the photocatalyst may become chemically active and effective to drive oxidation reactions with contaminants in the flowable medium in front of surface 101, thereby purifying the flowable medium.

Figure 2:
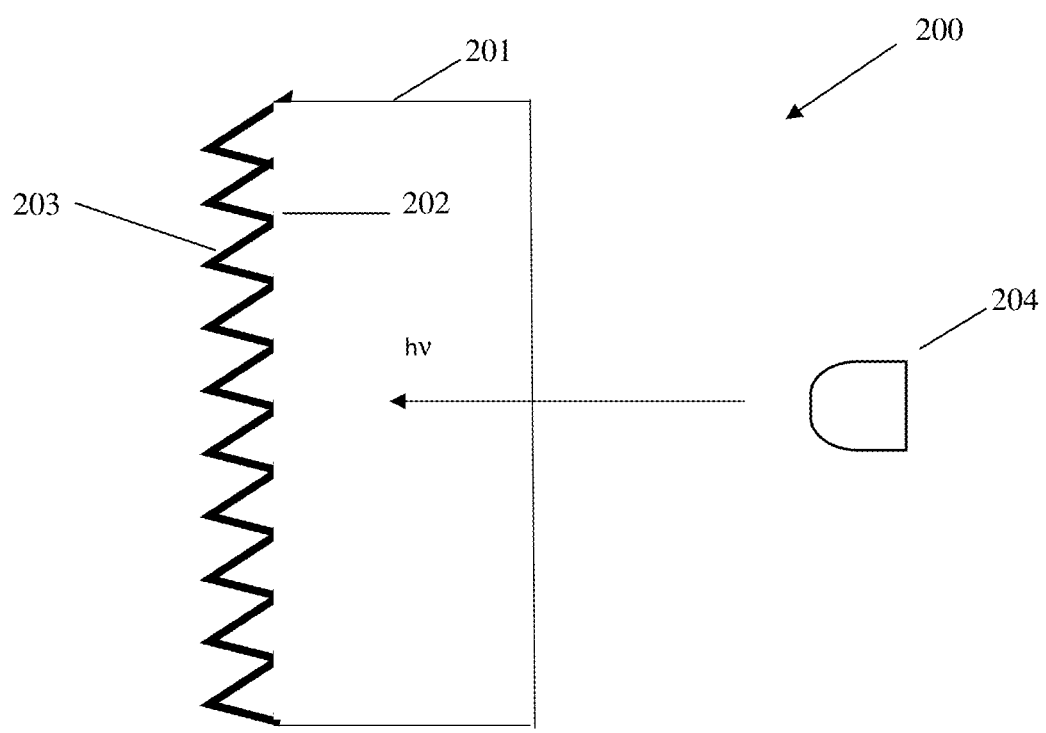
FIG. 2 is a schematic of back surface illuminated photocatalytic device, illustrating a conformal thin film photocatalytic material on a high surface area optically transmissive substrate.

FIG. 2 illustrates a similar configuration as FIG. 1 in which the transparent substrate 201 has had a surface 202 roughened, which has subsequently had the subject photocatalytic titania based thin film 203 formed on that surface with a high degree of conformality, composition and crystalline control. The material thickness may be accurately controlled as needed to allow the back surface illumination from source 204 to be absorbed throughout the layer 203 including in the proximity of its outer surface. Surfaces of this type may be used to increase the surface area of the photocatalytic surface and enhance the photocatalytic effect, thereby increasing the efficacy of the device to purify the ambient environment in front of photocatalytic surface 203.

Note that the substrate 201 may have its surface roughened 202, or the substrate surface may be flat and the surface of the photocatalytic film 203 may be roughened (not shown), or any combination thereof. The roughening of either the substrate or the film may be carried out by subtractive techniques, such as but not limited to, wet etching, dry etching, sanding, machining, or bead blasting. The roughening of either the substrate or the film may also be carried out by additive techniques such as, but not limited to, spray coating, powder coating, annealing, recrystallization, or nucleation or island formation before or during a thin film deposition process. Roughening may be in a nanoscale or microscale.

The present invention also includes formation of titania based materials on physically shaped or textured surfaces that have specific affinity or specific lethality for biologic impurities. For example certain micro topographies have been synthesized to mimic the topographic character of shark skin, resulting in corresponding antibacterial properties. Addition of the subject titania based photocatalytic materials to those surfaces will add an antiviral effect to that surface. Other engineered surface topographies may attract or bind specific viruses or bacteria based on the shape and spatial frequency power spectra of the surface topography. The subject titania photocatalytic materials and illumination schemes, or other photocatalytic materials, may be added to such surfaces to increase the microbe lethality and hence antimicrobial effects there. These antimicrobial effects may include prevention of biofilms or reduction of bioburden i.e. residual microbes and fomites present after other cleaning or disinfection processes. Such surfaces that combine microbe specific affinity surfaces with photocatalytic materials, may be used both as antimicrobial surfaces and for active purification surfaces in the subject fluid purification apparatuses of the subject invention.

Photocatalyst devices of this type may be used to purify air near medical instruments or other tools, or for example as wall panels in rooms in which the photocatalytic illumination is provide from behind the wall panel. It may also be used to purify the surfaces of those instruments, or other high touch surfaces in hospitals, home or in the workplace, to render them antimicrobial. Back surface illumination in those cases may be provided by near UV or visible light LEDs or other sources with adequate spectral irradiancy at suitable wavelengths to stimulate the photocatalytic effect.

Figure 3:
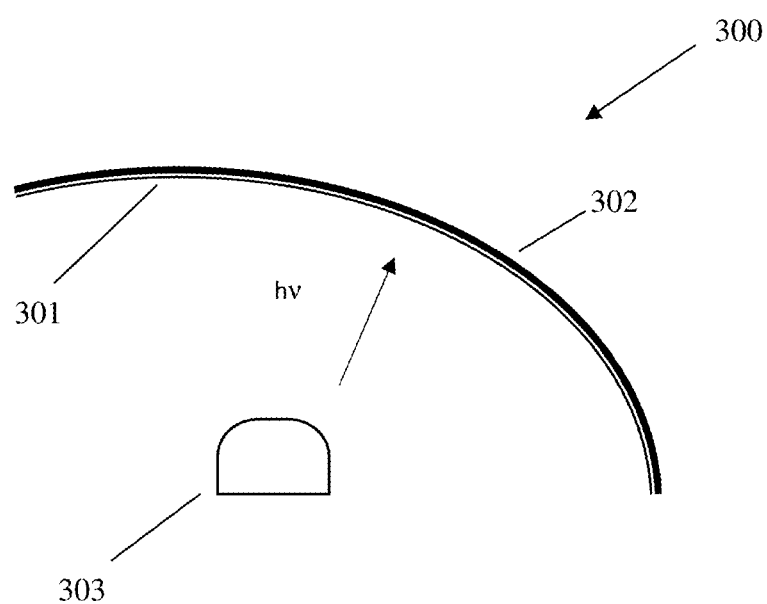
FIG. 3 is a schematic of a combined lighting and air purification system utilizing front surface illumination of the subject photocatalytic titania based material formed on a reflector.

FIG. 3 illustrates an embodiment combining a lighting and flowable media purification system utilizing front surface illumination of the subject photocatalytic titania based material formed on a reflector. In this embodiment 300, the titania based photocatalytic material 301 is applied to the front surface of a pure metallic or dielectric enhanced metallic reflective surface 302, and is illuminated by a broadband light source 303 such as a white LED that has significant optical emission in the UV or in the 400-450 nm. spectral regions. Alternatively the white light source may comprise any combination of red, green and blue wavelengths ("RGB"). While the metallic reflector has high reflectivity in the visible spectral region, the reflectivity and E-field characteristics of the reflector at the photocatalytic illumination wavelengths, and the thickness of the photocatalytic layer, may be optimized to enhance the photocatalytic effect, and hence the capability of the system to purify the flowable medium between the light 303 and the photocatalytic thin film 301.

Figure 4:
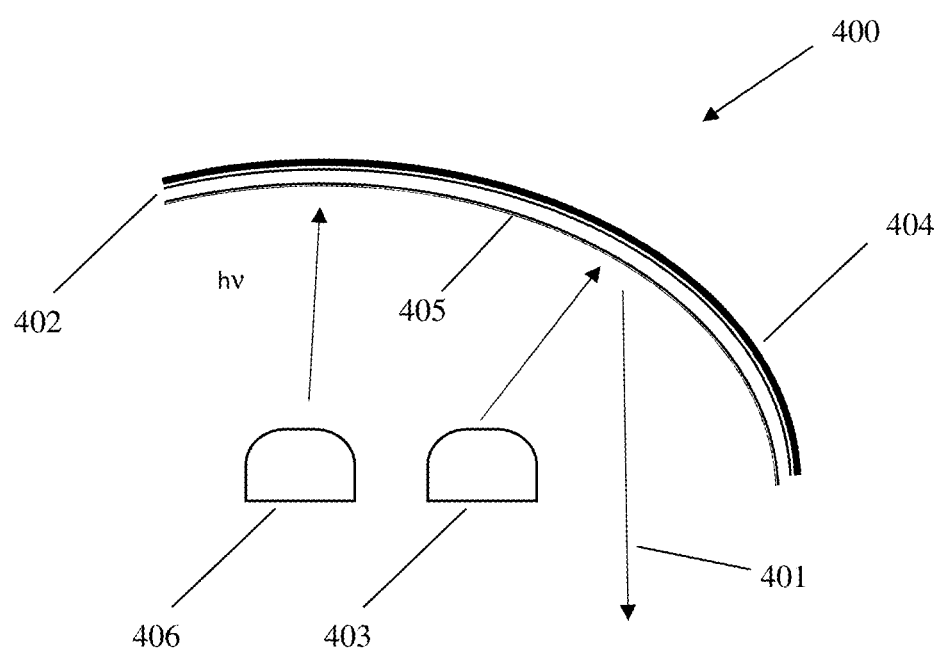
FIG. 4 is a schematic of a combined lighting and air purification system utilizing front surface illumination of the subject photocatalytic titania based material formed on a remote phosphor in an LED powered white light luminaire.

FIG. 4 illustrates a combined photocatalytic purifier and LED lighting system employing a titania based photocatalyst formed on a remote phosphor in an LED powered white light luminaire 400. In this case white light for illumination 401 is generated by irradiation of a remote phosphor layer 402 by a blue or UV light source 403. The remote phosphor layer 402 is interposed between the metallic or dielectric enhanced metallic high reflector 404, and titania based photocatalytic material 405. Alternatively the photocatalytic material 405 may be heterogeneously incorporated onto the surface of remote phosphor particles prior to their application in the luminaire system. Typically the short wavelength light source 403 for remote phosphor luminaires emits in the 460 nm. wavelength range. In cases where the photocatalytic effect at thin film 405 requires a different wavelength, a second source 406 may be included as needed to achieve the photocatalytic effect and purification of the flowable media at surface 405. The photocatalytic effecting source 403 may be operated intermittently, or during overnight hours for example as needed to regenerate the chemically active photocatalytic surface.

Figure 5:
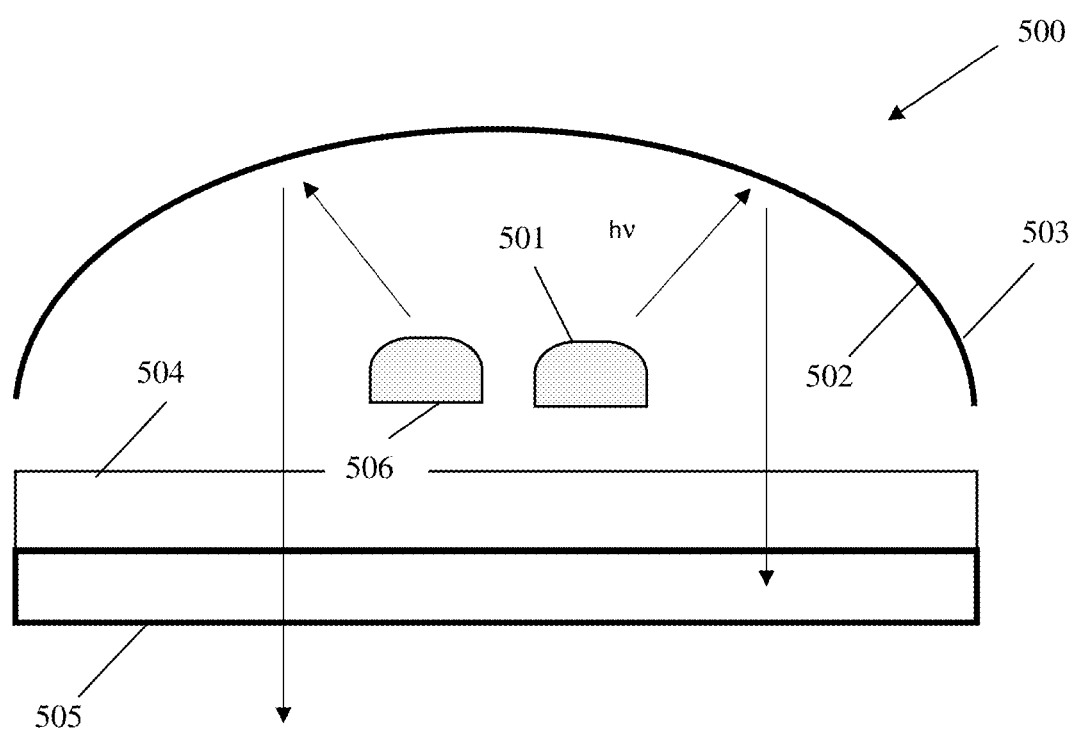
FIG. 5 is a schematic of a combined lighting and air purification system utilizing a predominantly white lighting luminaire and an optically transmissive element that supports the subject titania photocatalytic material.

FIG. 5 illustrates a flowable media purification function combined with a predominantly white lighting luminaire by utilizing a optically transmissive element that supports the subject titania photocatalytic material. One possible configuration for the luminaire has photocatalytic illumination hv from source 501 incident on a broadband luminaire metallic or dielectric enhanced metallic reflector 502 on a mechanical support 503. The reflector coating 502 has average reflectivity >80% in the visible spectral region (400-700 nm. wavelength), and >75% reflectivity for the photocatalytic illumination which may be UV (<400 nm. wavelength), or visible light, such as in the 400-500 nm portion of the visible spectrum. In a preferred embodiment, reflectivity is >90% in the visible spectral region (400-700 nm. wavelength), and >85% reflectivity for the photocatalytic illumination which may be UV (<400 nm. wavelength), or visible light, such as in the 400-500 nm. portion of the visible spectrum. In a further preferred embodiment, reflectivity is >95% in the visible spectral region (400-700 nm. wavelength), and >90% reflectivity for the photocatalytic illumination which may be UV (<400 nm. wavelength), or visible light, such as in the 400-500 nm. portion of the visible spectrum. Said reflected photocatalytic illumination is incident on a transmissive support 504 and then on the back surface of the photocatalytic material 505. Ambient flowable media at the front or outer facing surface of photocatalytic material 505 and is thereby purified by oxidizing chemical reactions.

White light illumination from source 506 is also incident on the reflector 502/503, and may be reflected through the transmissive element 504/505, for general illumination purposes. In another embodiment, a broadband antireflection coating may optionally be applied to the back surface of 504 to increase external transmittance of that element.

It is noted that for certain photocatalytic material compositions 505, visible light illumination will stimulate the photocatalytic effect, and in those cases the functions of sources 501 and 506 may be achieved by a single source or multiple sources of a single type.

Figure 6:
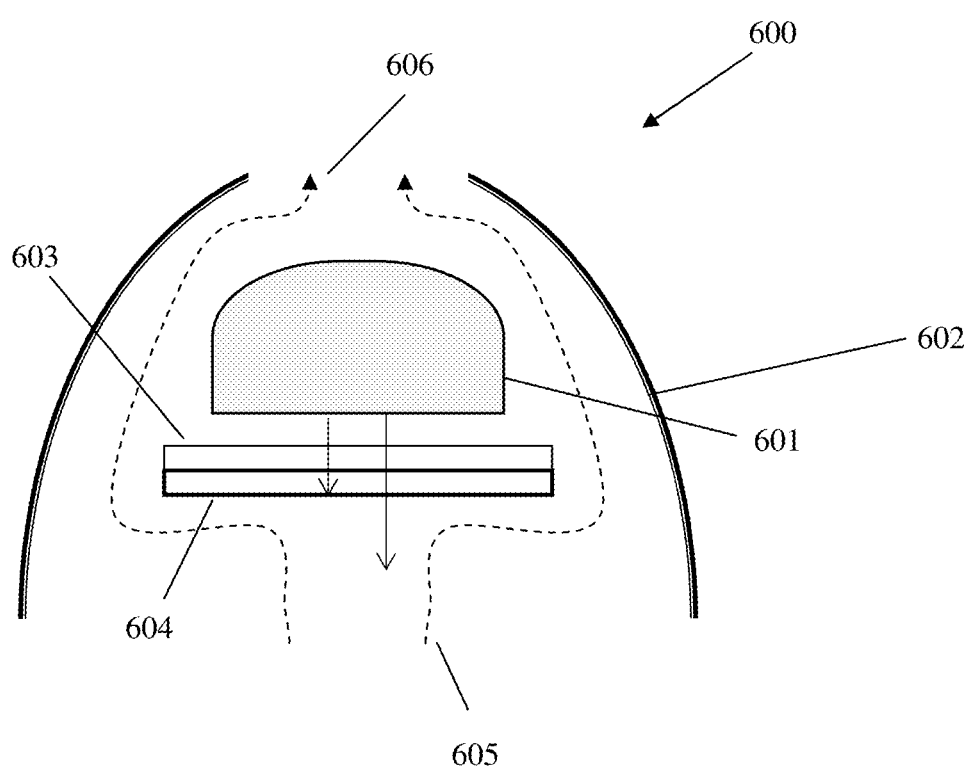
FIG. 6 is a schematic of a combined lighting and air purification system utilizing passive (i.e. convective) means to exchange ambient fluids during purification.

FIG. 6 shows a combined photocatalytic purifier and lighting system utilizing passive or convective means to exchange ambient fluids during purification. In an embodiment, a luminaire system 600 with light source 601 is used in a decorative and light directing enclosure 602. Illumination from 601 is incident on the back surface of the transmissive photocatalytic element 603 mounted on support or substrate 604, and said illumination serves as both general illumination and as illumination to stimulate the photocatalytic effect. In this case the titania based photocatalytic material is sensitive to visible light emitted by 601. In a preferred embodiment, ambient air 605 is drawn up to the photocatalytic surface, across its chemically active surface, and upwards through the lamp body. The purified air 606 exits the assembly. Said gas flow through the assembly is driven by convective forces via heating of the air around the light source 601, such as by waste heat from the source. Alternatively, if the support or substrate is transparent in the proper wavelength region, the photocatalytic material may be mounted on the side opposite the light source 601, facing the bottom opening of the enclosure 602, allowing the incoming air 605 to strike the photocatalytic material directly.

Figure 7:
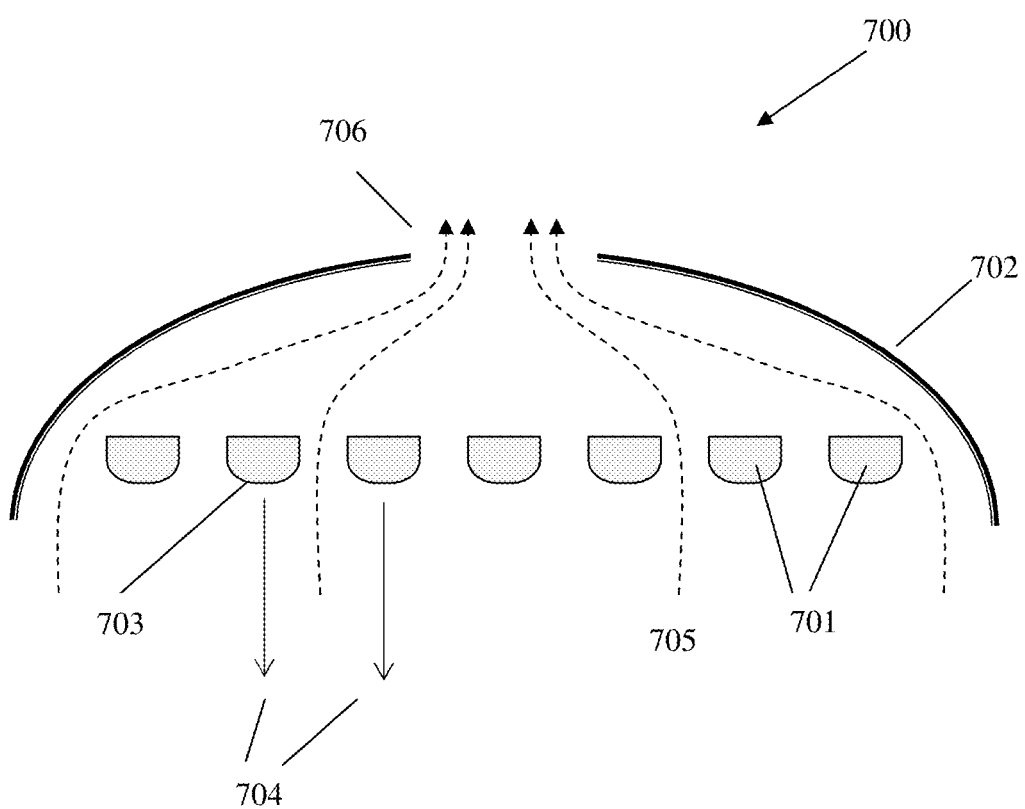
FIG. 7 is a schematic of a combined lighting and air purification system utilizing. an array of LED white light emitters in a decorative and light directing luminaire assembly.

FIG. 7 shows an embodiment 700 comprising an array of LED white light emitters 701 in a decorative and light directing luminaire assembly 702. The array is mounted on an air permeable packaging material. In this case the outer surface 703 of the LED emitters 701 has the subject titania based photocatalytic material incorporated thereon, and the composition of said material has been adjusted such that visible illumination from the white LEDs is suitable to stimulate the photocatalytic effect. White light general illumination 704 is generated by the luminaire. Ambient air 705 is drawn into, across and through the LED array by convective forces from waste heat from the LED array. In so doing it is purified by chemical reactions at the photocatalytic surfaces at each LED emitter. The purified air 706 passes upward and out of the top of the luminaire.

The subject invention may be embodied in the following examples that are by no means restrictive, but intended to illustrate the invention. It will be clear that the described invention is well adapted to achieve the purposes described above, as well as those inherent within. The citation of any publication is for its disclosure prior to the filing date and should not be construed as an admission that the present invention is not entitled to antedate such publication by virtue of prior invention. Numerous other changes may be made which will readily suggest themselves to those skilled in the art and which are encompassed both in the spirit of the disclosure above and the appended claims.

What is claimed is:

1. A flowable media purification apparatus comprising a photocatalytic thin film formed on a substrate, a constituent modifying two of the optical absorption, carrier recombination rate or photocatalytic characteristics of the thin film, a photocatalytic illumination light source, and provision for the flowable media to flow past the surface of the photocatalytic thin film material.

2. The apparatus of claim 1, wherein the photocatalytic thin film comprises titania.

3. The apparatus of claim 2, wherein the constituent in the photocatalytic thin film comprises an oxide of an element chosen from the group of La, Ce, Pr, Nd, Pm, Eu, Gd, Tb, Dy, Ho, Er, Tm, Yb, Co, W, V, W, Zr, Cu, Mn, Fe Cr or from the anion group of N or C.

4. The apparatus of claim 2, wherein the photocatalytic thin film incorporates metal particles, wherein the elements in the metal particles are chosen from the group of Pt, Pd, Ru, Ir, Ag, Cu, Au, and Fe.

5. The apparatus of claim 2, wherein the photocatalytic thin film has a thickness in the range of 1-30 nm.

6. The apparatus of claim 1, wherein the photocatalytic thin film has a thickness less than or equal to 5 times the optical skin depth of the light emitted by the light source which is of a suitable wavelength to stimulate photocatalysis within the thin film.

7. The apparatus of claim 1, wherein the surface area of the photocatalytic thin film is at least 1.5 times greater than it would be if the surface formed a simple geometric shape by using a combination of surface roughening and formation of the substrate into a complex geometric shape.

8. The apparatus of claim 7, wherein the complex geometric shape is formed from multiple fused capillary tubes.

9. The apparatus of claim 7, wherein the substrate is porous.

10. The apparatus of claim 1, wherein the thickness variation of the photocatalytic thin film is less than plus or minus 5% over the active surface of the photocatalytic thin film.

11. The apparatus of claim 1, wherein the substrate has disposed on it at least one coating to modify its optical properties.

12. The apparatus of claim 11, wherein the coating is chosen from the group of a metallic reflective layer, a dielectric enhanced metallic reflector, an all dielectric interference reflector, dichroic or band pass filter coating, an antireflection coating and a metal-dielectric band pass filter.

13. The apparatus of claim 12, wherein the light source may include a combination of geometric elements and reflective elements to achieve increased interaction distances in the thin film photocatalytic material.

14. The apparatus of claim 1, wherein the light source comprises a Light Emitting Diode.

15. The apparatus of claim 1, wherein the photocatalytic illumination light source comprises a light source for general illumination.

16. The apparatus of claim 15, wherein a separate non-illumination light source is incorporated to provide a suitable wavelength to stimulate photocatalysis within the thin film.

17. The apparatus of claim 15, wherein the light source which stimulates photocatalysis within the thin film is controlled according to a method chosen from the group of preprogrammed modulation schedules, motion detectors and other logical input.

18. The apparatus of claim 15, wherein the flowable media comprises air.

19. The apparatus of claim 18, wherein the substrate is structured in such a way as to cause the air to flow past the surface of the photocatalytic thin film primarily by means of convection.

20. The apparatus of claim 19, further comprising a high surface area substrate which serves as a heat dissipation surface.

21. The apparatus of claim 15, wherein the light source emits in the 400-470 nm wavelength range.

22. The apparatus of claim 15, wherein a wavelength converting phosphor is interposed in the optical path between the photocatalytic thin film and the light source.

23. The apparatus of claim 15, wherein the photocatalytic material is formed on the exterior envelope of an LED lamp.

24. The apparatus of claim 15, wherein the photocatalytic material is formed on one or more surfaces of an LED luminaire.

25. A flowable media purification apparatus comprising a photocatalytic thin film disposed over a substrate, a light source capable of illuminating the photocatalytic thin film in the 305-470 nm range, and provision for the flowable media to flow past the surface of the photocatalytic thin film.

26. The apparatus of claim 25, comprising a light source, wherein the light wavelengths from the photocatalytic illumination source are between 400 and 470 nm.

27. The apparatus of claim 25, comprising a substrate with a high degree of open cell porosity.

28. The apparatus of claim 27, wherein the high porosity substrate has a surface area greater than 50 square meters per gram.

29. The apparatus of claim 27, wherein the flowable media flows primarily in one direction through the high porosity substrate.

30. The apparatus of claim 25, comprising one or more optical means to substantially confine the photocatalytic illumination in the photocatalytic thin film disposed on the high porosity substrate.

31. The apparatus of claim 30, wherein the optical confining means include reflective surfaces, waveguides or total internal reflection.

32. A biologically surface sterilizing apparatus, comprising; a photocatalytic thin film formed on a substrate, the photocatalytic thin film comprising titanium oxide and constituents that modify two of the optical absorption, carrier recombination rate, photocatalytic characteristics of the thin film, or antimicrobial characteristics of the film, and a light source which stimulates photocatalysis in the thin film.

33. The apparatus of claim 32, wherein the photocatalytic illumination source is an LED that emits in the 380-470 nm spectral band.

34. The apparatus of claim 32, wherein the substrate has surface features or topography engineered to provide affinity or lethality for bacteria or viruses.

35. The apparatus of claim 32, wherein the photocatalytic thin film comprising titanium oxide has been compositionally modified to increase its abrasion resistance, hardness or chemical resistance.

36. The apparatus of claim 35, wherein the photocatalytic titanium oxide thin film has been modified with aluminum oxide, silicon oxide, or zirconium oxide.

37. The apparatus of claim 32, wherein the photocatalytic titanium oxide thin film has been modified with Cu or Ag particles exposed on the surface of the photocatalytic thin film.

38. The apparatus of claim 32, which has been incorporated in the surface of high touch objects.

* * * * *